United States Patent
Wang et al.

(10) Patent No.: US 11,911,538 B2
(45) Date of Patent: Feb. 27, 2024

(54) INSTANTANEOUS STERILIZATION SYSTEM FOR VENTILATION AND AIR CONDITIONING

(71) Applicants: Quanling Wang, Hebei (CN); Miaohong Wang, Hebei (CN)

(72) Inventors: Quanling Wang, Hebei (CN); Miaohong Wang, Hebei (CN)

(*) Notice: Subject to any disclaimer, the term of this patent is extended or adjusted under 35 U.S.C. 154(b) by 0 days.

(21) Appl. No.: 18/056,707

(22) Filed: Nov. 17, 2022

(65) Prior Publication Data

US 2023/0083721 A1    Mar. 16, 2023

Related U.S. Application Data

(63) Continuation of application No. PCT/CN2021/000061, filed on Apr. 8, 2021.

(30) Foreign Application Priority Data

Apr. 8, 2020 (CN) .......................... 202010269918.1
Apr. 8, 2020 (CN) .......................... 202010270333.1

(51) Int. Cl.
    *A61L 9/014*      (2006.01)
    *A61L 9/04*      (2006.01)
    (Continued)

(52) U.S. Cl.
    CPC ............... *A61L 9/014* (2013.01); *A61L 9/046* (2013.01); *A61L 9/122* (2013.01); *A61L 9/14* (2013.01);
    (Continued)

(58) Field of Classification Search
None
See application file for complete search history.

(56) References Cited

U.S. PATENT DOCUMENTS

2005/0129571 A1    6/2005   Centanni

FOREIGN PATENT DOCUMENTS

CN      101646466 A      2/2010
CN      102297489 A     12/2011
(Continued)

OTHER PUBLICATIONS

Jung, S. KR20090044661A—translated document (Year: 2009).*
(Continued)

*Primary Examiner* — Jelitza M Perez

(57) ABSTRACT

An instantaneous sterilization system for ventilation and air conditioning comprises: an air inlet; an instantaneous sterilization device being one or more of a chlorine dioxide disinfector, a hydrogen peroxide or hydrogen peroxide silver ion disinfector, an ultraviolet disinfector, an ULPA ultra-efficient air filter, a HEPA high efficiency particle air filter, a laser disinfector, a microwave disinfector, an infrared disinfector, an X-ray disinfector and a γ-ray disinfector, an output end of the instantaneous sterilization device being provided with a sterilized air outlet, and the sterilized air outlet being communicated with air and serves as an output end of the instantaneous sterilization system for ventilation and air conditioning; and a fan, an air inlet end of the fan being connected with the air inlet, and an air exhaust end of the fan being connected with the input end of the instantaneous sterilization device.

1 Claim, 30 Drawing Sheets

(51) Int. Cl.
  *A61L 9/12* (2006.01)
  *A61L 9/14* (2006.01)
  *A61L 9/20* (2006.01)
  *F24F 8/108* (2021.01)
  *A61L 101/06* (2006.01)

(52) U.S. Cl.
  CPC ............... *A61L 9/20* (2013.01); *F24F 8/108* (2021.01); *A61L 2101/06* (2020.08); *A61L 2209/132* (2013.01); *A61L 2209/134* (2013.01); *A61L 2209/14* (2013.01); *A61L 2209/16* (2013.01); *A61L 2209/21* (2013.01); *F24F 2221/225* (2013.01)

(56) References Cited

FOREIGN PATENT DOCUMENTS

| | | | |
|---|---|---|---|
| CN | 103868156 A | * | 6/2014 |
| CN | 103868156 A | | 6/2014 |
| CN | 203837106 U | | 9/2014 |
| CN | 203837130 U | | 9/2014 |
| CN | 105003991 A | | 10/2015 |
| CN | 109908390 A | | 6/2019 |
| CN | 111351159 A | | 6/2020 |
| CN | 111351160 A | | 6/2020 |
| KR | 20090044661 A | * | 2/2009 |

OTHER PUBLICATIONS

EPA-What is a HEPA filter? Indoor Air Quality. United States Environmental Protection Agency. pp. 1-3. https://www.epa.gov/indoor-air-quality-iaq/what-hepa-filter#:~:text=This%20type%20of%20air%20filter,penetrating%20particle%20size%20(MPPS). (Year: 2023).*

Zhou, Q. (CN103868156A)—translated document (Year: 2014).*

Internation Search Report of PCT/CN2021/000061, dated Jun. 28, 2021.

* cited by examiner

INSTANTANEOUS STERILIZATION SYSTEM FOR VENTILATION AND AIR CONDITIONING

This application claims the priority of the Chinese patent applications filed on Apr. 8, 2020, with the application numbers of 202010269918.1 and 202010270333.1, the entire contents of which are hereby incorporated by reference.

TECHNICAL FIELD

The application relates to the technical field of ventilation and air conditioning systems, for example, relates to an instantaneous sterilization system for ventilation and air conditioning.

BACKGROUND

Ventilation and air conditioning systems have spread in all large and small buildings. Ventilation and air conditioning systems all adopt ventilation pipelines to circulate air. Because the pipelines are inconvenient to clean and disinfect manually, bacteria and viruses may survive and propagate in the pipelines after long-term operation, particularly, a large amount of bacteria and viruses in ventilation pipelines which operate for many years are propagated and circulated in the air in the period of high incidence of influenza viruses, so that the health of human bodies is seriously influenced.

The coronavirus epidemic has spread to all countries in the world. High efficiency particle air filters can block the bacteria in the high efficiency particle air filters temporarily through a separation mode, and prevent the bacteria from passing through the high efficiency particle air filters. However, with the increase of operating time, the bacteria may breed on the high efficiency particle air filters and dust in the high efficiency particle air filters may enlarge the wind resistance of the high efficiency particle air filters, so the high efficiency particle air filters need often to replace frequently. The replacement increases the opportunity of secondary pollution. Although enzyme sterilization high efficiency particle air filters are used as filtering materials, there are no reports of killing HIV, influenza virus, SARS coronavirus, Ebola virus, avian influenza virus and Covid-19, and it is impossible to realize a replacement-free and maintenance-free unmanned operation scene, and the cost is high. Although chemical disinfectants, ultraviolet ray and ozone disinfecting devices can effectively kill the bacteria and the viruses, a certain disinfection time is needed, particularly, ultraviolet ray lamp tubes must directly irradiate a surface of a disinfected object, and the irradiation disinfection time should be at least six minutes to effectively kill the bacteria and viruses. The ozone also requires a disinfection time of at least fifteen minutes or more, and is less able to kill the bacteria and viruses instantaneously. In the related art, wind speeds of the ventilation and air conditioning systems are basically designed to be about 3 m/s to 15 m/s, that is, virus-carrying air passes through air conditioning disinfecting devices within about one to three seconds. Therefore, when the air containing bacteria and viruses passes through the ultraviolet and ozone disinfection devices instantaneously, the bacteria and the viruses cannot be killed within one to three seconds. Although the ozone can kill the bacteria and viruses, the ozone can cause serious harm to the human bodies, particularly to respiratory tracts, so that the ozone cannot be applied to ventilation and air conditioning systems operated in a manned place, and can only disinfect air conditioning pipeline systems in an unmanned condition. Especially, hospitals are equipped with a large number of ultraviolet disinfection lamps, and the ultraviolet disinfection lamps can only be used for disinfection without people, otherwise the ultraviolet rays will seriously harm the human bodies, especially eyes. In conclusion, the above disinfection technologies and products cannot be operated in a manned occasion such as hospitals, office buildings, shopping malls and theaters. Therefore, the research and development of technologies and products of instantaneous and real-time disinfection human-co-existed devices for killing bacteria and viruses are at the forefront of ventilation technologies. It is urgent for the world's scientific and technical personnel to develop an instantaneous sterilization device for ventilation and air conditioning systems and a harmless air discharge system for negative pressure hospitals and ambulances, which can effectively ensure the safety of the atmosphere and urban environment while rescuing virus carriers.

The smallest particle size of virus particles is 0.018-0.02 μm, while the largest particle size of virus particles, for example, animal pox virus, is about 0.17-0.26 μm, and some viruses have a larger particle size of 0.3-0.45 μm. The foot-and-mouth disease has a particle size of only 0.01 μm, which is the smallest particle size in the world. For common influenza viruses, the influenza A (H1N1) virus has a particle size of 0.09 μm, the Ebola virus has a particle size of 0.08 μm, the Sars virus has a particle size of 0.06-0.22 μm, and the novel coronavirus has a particle size of 0.06-0.14 μm. Most of bacteria have a particle size of 0.5-5 μm, and the smallest bacteria have a particle size of 0.2 μm. In conclusion, the HEPA high efficiency particle air filters can only instantaneously block bacteria having a particle size larger than or equal to 0.3 μm, but cannot block bacteria having a particle size smaller than or equal to 0.3 μm, and cannot block viruses having a particle size of 0.01-0.3 μm. ULPA ultra-efficient air filters can effectively filter out particulate matters with a particle size of 0.01-0.3 μm, and viruses are blocked and cannot pass through the ULPA ultra-efficient air filters. However, the bacteria and viruses accumulate on surfaces of the filter elements of the ultra-efficient air filters for a long time and breed greatly, which is a very dangerous pollution source for the ventilation and air conditioning systems. Although bacteriostatic materials are employed in the HEPA high efficiency particle air filters, the related art only inhibits the propagation of the bacteria but cannot inhibit the viruses. Therefore, the ULPA ultra-efficient air filters and the HEPA high efficiency particle air filters can block the bacteria and the viruses instantaneously, but cannot kill the virus particles and prevent the propagation of the viruses. Therefore, the ULPA ultra-efficient air filters and the HEPA high efficiency particle air filters can only filter the bacteria and the viruses, but cannot sterilize the bacteria and the viruses.

SUMMARY

The present application provides an instantaneous sterilization system for ventilation and air conditioning, which can solve the difficult problems and application of instantaneous sterilization technologies in the related art.

An embodiment provides an instantaneous sterilization system for ventilation and air conditioning, comprising: an air inlet, the air inlet being communicated with air and configured to be an input end of the instantaneous sterilization system for ventilation and air conditioning; an instantaneous sterilization device being one or more of a chlorine dioxide disinfector, a hydrogen peroxide or hydrogen peroxide silver ion disinfector, an ultraviolet disinfector, an ULPA ultra-efficient air filter, a HEPA high efficiency particle air filter, a laser disinfector, a microwave disinfector, an infrared disinfector, an X-ray disinfector and a γ-ray disinfector, the air inlet being configured at an input end of the instantaneous sterilization device, an output end of the instantaneous sterilization device being provided with a sterilized air outlet, the sterilized air outlet being configured at the output end of the instantaneous sterilization device, and the sterilized air outlet being communicated with the air and serves as an output end of the instantaneous sterilization system for ventilation and air conditioning; and a fan, an air inlet end of the fan being connected with the air inlet, and an air exhaust end of the fan being connected with the input end of the instantaneous sterilization device.

Figure 1:
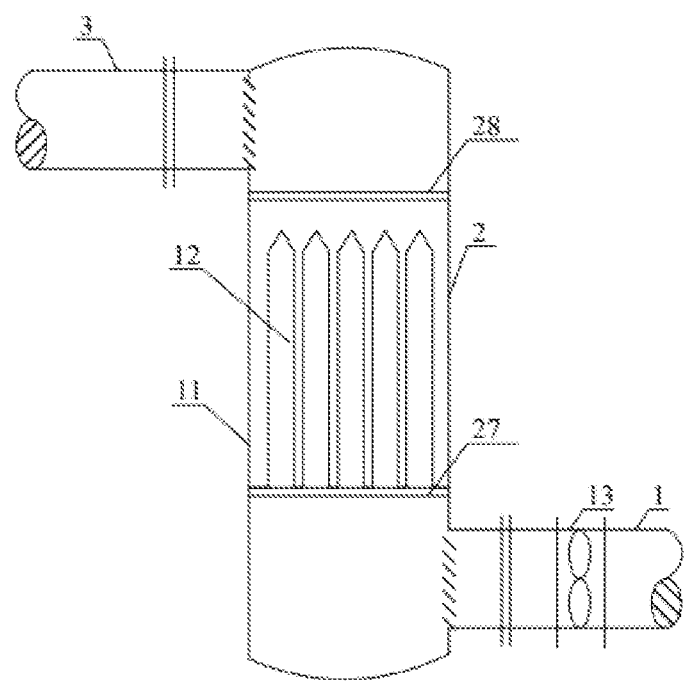
FIG. 1 is a schematic diagram of an instantaneous sterilization device provided by an embodiment of the present application.

1 refers to air inlet; 2 refers to instantaneous sterilization device; 3 refers to sterilized air outlet; 4 refers to clean water spray pump; 5 refers to water-washing spray pipe; 6 refers to water-washing nozzle; 7 refers to spray pump; 8 refers to spray pipe; 9 refers to nozzle; 10 refers to dioxide peroxide spray liquid; 11 refers to ULPA ultra-efficient air filter; 12 refers to ULPA ultra-efficient filter element; 13 refers to fan; 14 refers to pipeline air-liquid mixer; 15 refers to ultrasonic atomizer; 16 refers to ultrasonic generator; 17 refers to air pipe; 18 refers to Venturi air-liquid mixer; 19 refers to Venturi circulating pump; 20 refers to Venturi pump circulating pipe; 21 refers to Venturi intakeport; 22 refers to primary filter; 23 refers to primary filter element screen; 24 refers to air-liquid mixer interface; 25 refers to immersion air-liquid mixer; 26 refers to microporous air-liquid mixer; 27 refers to air inlet of ULPA filter; 28 refers to air outlet of ULPA filter; 29 refers to ultraviolet sterilizing device; 30 refers to ultraviolet lamp tube; 31 refers to water-washing type spray device; 32 refers to clean water; 33 refers to clean water spray liquid; 34 refers to clean-water spray air inlet; 35 refers to tap water interface; 36 refers to waste liquid discharge port; 37 refers to air-water separating device; 38 refers to clean-water spray air outlet; 39 refers to air pipe check valve; 40 refers to disinfectant sprinkling device of atmosphere disinfecting track; 41 refers to disinfectant atomization device of atmosphere disinfecting track; 42 refers to disinfectant spraying device of atmosphere disinfecting track; 43 refers to spray damping filler; 44 refers to hydrogen peroxide silver ion liquid device; 45 refers to hydrogen peroxide silver ion liquid; 46 refers to hydrogen peroxide silver ion liquid automatic adding and proportioning device; 47 refers to hydrogen peroxide silver ion solution; 48 refers to hydrogen peroxide silver ion spray liquid; 49 refers to HEPA high efficiency particle air filter; 50 refers to HEPA filter element screen; 51 refers to air inlet of HEPA filter; 52 refers to air outlet of HEPA filter; 53 refers to fresh air inlet; 54 refers to fresh air fan; 55 refers to fresh air outlet; 56 refers to instantaneous sterilization system air inlet; 57 refers to instantaneous sterilization system air outlet; 58 refers to instantaneous sterilization system; 59 refers to fresh air pipeline inlet; 60 refers to fresh air pipeline; 61 refers to fresh air outlet; 62 refers to building; 63 refers to building door and window; 64 refers to air-conditioning unit air inlet; 65 refers to air-conditioning unit; 66 refers to air-conditioning unit air outlet; 67 refers to sterilization air-conditioning air-inlet interface; 68 refers to air-conditioning air-delivery duct; 69 refers to air-conditioning air port; 70 refers to sterilization air-conditioning room air-return port; 71 refers to sterilization air-conditioning house; 72 refers to negative-pressure harmless ambulance; 73 refers to ambulance negative-pressure cabin; 74 refers to negative-pressure ambulance air inlet; 75 refers to ventilation dust filtrating screen; 76 refers to ambulance air-conditioning surface cooler; 77 refers to negative-pressure ambulances air-conditioning air port; 78 refers to ambulance negative-pressure cabin door; 79 refers to negative-pressure ambulances harmless air outlet; 80 refers to negative-pressure harmless contagious ward; 81 refers to contagious ward air inlet; 82 refers to contagious ward air-intake duct check valve; 83 refers to contagious ward air conditioning air-delivery duct; 84 refers to contagious ward air-return port check valve; 85 refers to contagious ward air-conditioning air outlet port; 86 refers to contagious ward air-conditioning air-return port; 87 refers to contagious ward air-conditioning air-return duct; 88 refers to contagious ward air-return duct check valve; 89 refers to contagious ward air-conditioning air-return port check valve; 90 refers to negative-pressure harmless contagious ward air-return interface; 91 refers to main air inlet interface; 92 refers to medium-efficiency filter; 93 refers to medium-efficiency filter element screen; 94 refers to heat pump refrigeration compressor; 95 refers to four-way reversing valve; 96 refers to condenser/evaporator; 97 refers to expansion valve; 98 refers to evaporator/condenser; 99 refers to energy storage tank; 100 refers to air-conditioning energy-storage water pump; 101 refers to heat-recovery heat exchanger; 102 refers to heat-recovery circulating pump; 103 refers to heat-recovery water-supply interface; 104 refers to heat-recovery water-return interface; 105 refers to air-conditioning output circulating pump; 106 refers to air-conditioning output circulating water-return interface; 107 refers to air-conditioning fresh air handling unit; 108 refers to surface cooler of air-conditioning fresh air handling unit; 109 refers to water-inlet interface of surface cooler of air-conditioning fresh air handling unit; 110 refers to water-return interface of surface cooler of air-conditioning fresh air handling unit; 111 refers to air inlet of air-conditioning fresh air handling unit; 112 refers to air inlet of air-conditioning fresh air handling unit; 113 refers to air-outlet interface of air-conditioning fresh air handling unit; 114 refers to heat-recovery device; 115 refers to heat-recovery surface cooler; 116 refers to heat-recovery air inlet; 117 refers to heat-recovery air outlet; 118 refers to water-inlet interface of heat-recovery surface cooler; 119 refers to water-return interface of heat-recovery surface cooler; 120 refers to domestic hot water heat exchanger; 121 refers to domestic hot water heat-storage pump; 122 refers to domestic water storage tank; 123 refers to domestic hot water supply interface; 124 refers to tap water interface; 125 refers to solution immersion heat exchanger; 126 refers to water-inlet interface of immersion heat exchanger; 127 refers to water-outlet interface of immersion heat exchanger; 128 refers to solution plate heat exchanger; 129 refers to solution heat exchanger circulating pump; 130 refers to secondary circulating water inlet of plate heat exchanger; 131 refers to secondary circulating water outlet of plate heat exchanger; 134 refers to atmosphere disinfecting track; 135 refers to chassis of atmosphere disinfecting track; 136 refers to door of atmosphere disinfecting track equipment room; 137 refers to air inlet of atmosphere disinfecting track; 138 refers to air-inlet interface of atmosphere disinfecting track; 139 refers to air outlet of atmosphere disinfecting track; 140 refers to air-outlet interface of atmosphere disinfecting track; 141 refers to disinfectant sprinkling device; 142 refers to disinfectant spraying equipment box; 143 refers to disinfectant spraying device; 144 refers to microwave disinfecting device; 145 refers to microwave generator; 146 refers to laser disinfecting device; 147 refers to laser generator; 148 refers to X-ray disinfecting device; 149 refers to X-ray generator; 150 refers to γ-ray disinfecting device; 151 refers to γ-ray generator; 152 refers to booster fan; 153 refers to infrared disinfecting device; 154 refers to infrared generator; 600 refers to dioxide peroxide solution; 220 refers to dioxide peroxide generator; 230 refers to dioxide peroxide liquid; 400 refers to dioxide peroxide device; 410 refers to dioxide peroxide preparation device; 500 refers to dioxide peroxide solution; 440 refers to dioxide peroxide addition door; and 420 refers to dioxide peroxide liquid automatic adding and proportioning device.

DETAILED DESCRIPTION

As shown in FIG. 1, FIG. 1 is a schematic diagram of an instantaneous sterilization system for ventilation and air conditioning provided by an embodiment of the present application. In FIG. 1, the instantaneous sterilization system for ventilation and air conditioning comprises an air inlet 1, an instantaneous sterilization device 2, a sterilized air outlet 3 and a fan 13. The instantaneous sterilization device may be an ULPA ultra-efficient air filter or a HEPA high efficiency particle air filter. In FIG. 1, contaminated air passes through the fan 13 via the air inlet 1, and bacteria and virus particles are blocked and filtered by an air inlet 27 of the HEPA filter or an air inlet 51 of the HEPA filter and an ULPA ultra-efficient filter element 12 or a HEPA filter element screen 50, so that the virus particles cannot pass through the ULPA ultra-efficient filter element 12 or the HEPA filter element screen 50, and the sterilized air is discharged through an air outlet 28 of the ULPA filter or an air outlet 52 of the HEPA filter and then is output from the sterilized air outlet 3.

In one embodiment, the instantaneous sterilization device of FIG. 1 may also be a chlorine dioxide disinfector or a hydrogen peroxide silver ion disinfector, which destroys viral nucleic acids by strong oxidation of a chlorine dioxide disinfectant or a hydrogen peroxide silver ion disinfectant to achieve sterilization.

In one embodiment, the instantaneous sterilization device 2 of FIG. 1 may also be an ultraviolet disinfection disinfector, which can catalyze and decompose bacteria and viruses by ultraviolet rays to achieve sterilization.

In one embodiment, the instantaneous sterilization device of FIG. 1 may also be one of a laser disinfector, a microwave disinfector, or an infrared disinfector, which utilizes instantaneous dry heat functions of microwave, laser or infrared rays to destroy virus nucleic acid, thereby achieving the effect of killing virus spores.

In one embodiment, the instantaneous sterilization device 2 of FIG. 1 may also be one of an X-ray disinfecting device and a γ-ray disinfecting device, which utilizes the X-rays or γ-rays to penetrate through germ spores and fungal spores instantaneously to completely kill bacteria or viruses, thereby achieving sterilization.

Figure 2:
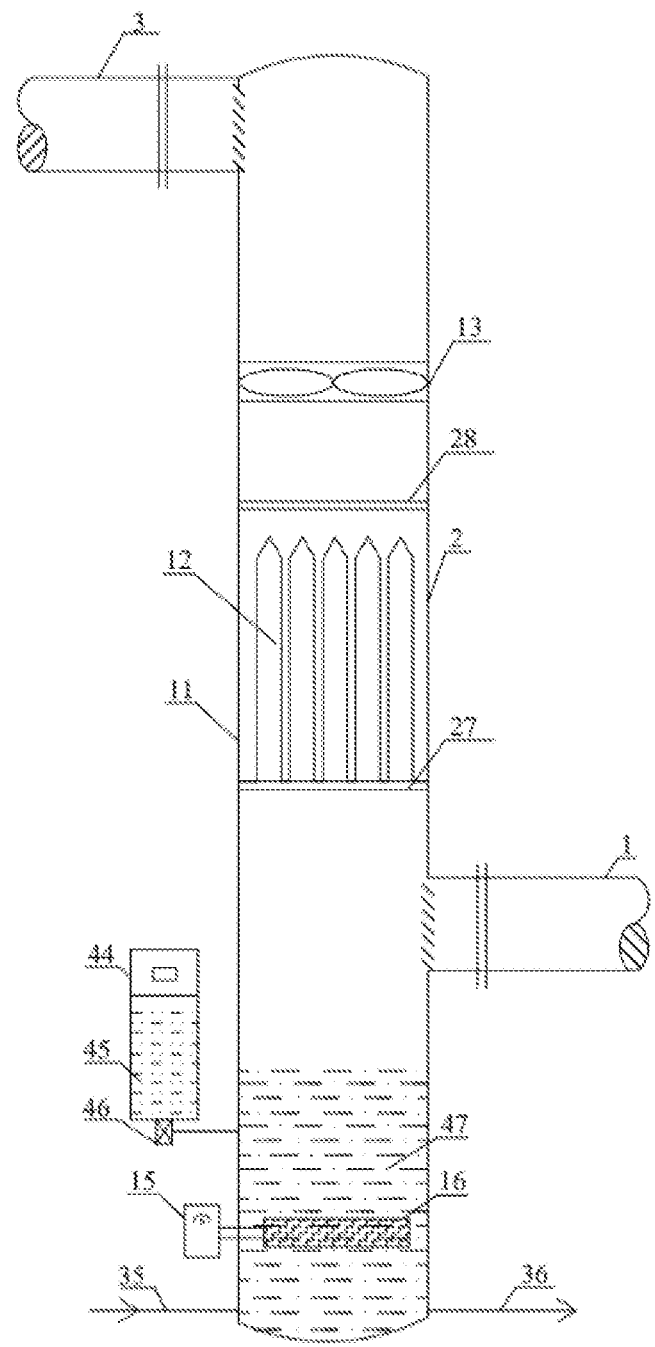
FIG. 2 is a schematic diagram of the instantaneous sterilization device provided by the present application, which adopts an ULPA ultra-efficient air filter or a HEPA high efficiency particle air filter and is configured with hydrogen peroxide silver ion spray.

In FIG. 2, the instantaneous sterilization system for ventilation and air conditioning comprises an air inlet 1, an instantaneous sterilization device 2, a sterilized air outlet 3, a fan 13, an ultrasonic atomizer 15, an ultrasonic generator 16, an ULPA ultra-efficient air filter 11 or a HEPA high efficiency particle air filter 49, and a hydrogen peroxide silver ion liquid device 44, wherein a hydrogen peroxide silver ion liquid 45 and a hydrogen peroxide silver ion solution 47 are added in the instantaneous sterilization system for ventilation and air conditioning. One of the ULPA ultra-efficient air filter 11 and the HEPA high efficiency particle air filter 49 is arranged in the instantaneous sterilization device 2.

In FIG. 2, contaminated air is forced to pass through the air inlet 27 of the HEPA filter or the air inlet 51 of the HEPA filter by the air inlet 1 through the fan 13, bacteria and virus particles are blocked and filtered by the ULPA ultra-high efficiency particle air filter element 12 or the HEPA filter element screen 50, so that the virus particles cannot pass through the ULPA ultra-efficient filter element 12 or the HEPA filter element screen 50, and the sterilized air is discharged from the air outlet 28 of the ULPA filter or the air outlet 52 of the HEPA filter and then is output from the sterilized air outlet 3. The ULPA ultra-efficient filter element 12 can filter viruses of 0.01-0.3 μm, and can reach a purification accuracy of 99.9995%. The HEPA filter element screen 50 mainly traps virus particles no less than 0.5 μm, and a filtering efficiency of the HEPA filter element screen 50 is above 99.97%. Although the ULPA ultra-efficient air filter can effectively filter out virus particles of 0.01-0.3 μm and the HEPA filter element screen 50 can trap bacterial particles no less than 0.5 the viruses are blocked and cannot pass through the ULPA ultra-efficient air filter 11 or the HEPA high efficiency particle air filter 49, and the bacteria and the viruses are accumulated on a surface of the ULPA ultra-efficient filter element 12 or the HEPA filter element screen 50 for a long time and are propagated in large quantities, which is a very dangerous pollution source for the ventilation and air conditioning systems. Therefore, the ULPA ultra-efficient air filter 11 and the HEPA high efficiency particle air filter 49 can instantaneously block the bacteria and the viruses, but cannot kill the bacteria and the viruses.

The hydrogen peroxide silver ion liquid device is arranged in the instantaneous sterilization device 2, the hydrogen peroxide silver ion liquid device 44 is added with a hydrogen peroxide silver ion liquid automatic adding and proportioning device 46. The hydrogen peroxide silver ion liquid 45 is provided to the instantaneous sterilization device 2 by providing the hydrogen peroxide silver ion liquid 45 in the hydrogen peroxide silver ion liquid device 44 and through the hydrogen peroxide silver ion liquid automatic adding and proportioning device 46. The ultrasonic atomizer 15 and the ultrasonic generator 16 are also arranged in the instantaneous sterilization device 2. The ultrasonic atomizer 15 outputs an ultrasonic frequency current, and the current is led into piezoelectric ceramic in the ultrasonic generator 16. The piezoelectric ceramic generates ultrasonic vibration according to the ultrasonic frequency current input by the ultrasonic atomizer 15, so that the hydrogen peroxide silver ion solution 47 around the ultrasonic generator 16 is ultrasonically atomized, and the hydrogen peroxide silver ion solution 47 is atomized to generate a large amount of molecular drift of the hydrogen peroxide silver ions which are distributed on the surface of the ULPA ultra-efficient air filter 12 of the ULPA ultra-efficient air filter or the surface of the HEPA filter element screen 50 of the HEPA high efficiency particle air filter through the air inlet 27 of the HEPA filter or the air inlet 51 of the HEPA filter, as the hydrogen peroxide silver ion is recognized as the safest disinfectant for killing virus spores in the world, and is a disinfection product harmless to human body. A large number of bacteria and viruses accumulated on the surface of the ULPA ultra-efficient filter element 12 of the ULPA ultra-efficient air filter 11 or the HEPA filter element screen 50 of the HEPA high efficiency particle air filter 49 are killed after contacting with a large number of hydrogen peroxide silver ions generated by atomization. Although the virus cannot be killed instantaneously, due to the instantaneous filtering and blocking effect of the ULPA ultra-efficient air filter 11 or the HEPA high efficiency particle air filter 49, a large amount of trapped bacterial and virus particles are inactivated by the hydrogen peroxide silver ions within a certain disinfection time to achieve instantaneous sterilization. The above disinfection and sterilization process is the principle of instantaneous sterilization by using the ULPA ultra-efficient air filter 11 or the HEPA high efficiency particle air filter 49 combined with the hydrogen peroxide silver ions for disinfection according to the present application. The fan 13 is configured between the air outlet 28 of the ULPA ultra-efficient air filter and the sterilized air outlet 3, or between the air outlet 52 of the HEPA filter and the sterilized air outlet 3, which has the same function as that of the fan 13 configured between the air inlet 1 and the air inlet 27 of the HEPA filter or the air inlet 51 of the HEPA filter in FIG. 1. When the fan 13 is close to the ULPA ultra-efficient air filter 11 or the HEPA high efficiency particle air filter 49, the fan 13 is selectively configured at the air outlet 28 of the ULPA ultra-efficient air filter or the air outlet 52 of the HEPA filter to prevent an impact of an airflow on the filters, and finally, the sterilized clean air is discharged from the sterilized air outlet 3. The structure shown in FIG. 2 is simple, and is suitable for families with small ventilation, negative-pressure ambulances, single negative-pressure contagious wards, and various vehicles.

In the related art, the hydrogen peroxide silver ion disinfection products are all liquid, hydrogen peroxide silver ion liquid 45 is internally provided with the hydrogen peroxide silver ion liquid device 44, and the hydrogen peroxide silver ion liquid 45 is automatically monitored and added to the instantaneous sterilization device 2 through the hydrogen peroxide silver ion liquid automatic adding and proportioning device 46. The water supplemented into the tap water interface 35 shown in FIG. 2 to FIG. 31 of the present application is purified water, instead of tap water. Because the tap water in China and the United States is disinfected with chlorine dioxide, the tap water contains chlorine, and the hydrogen peroxide silver ions will chemically react with chlorine, so the hydrogen peroxide silver ion solution 47 cannot be filled with tap water, but needs to be filled with purified water. In EU countries, the tap water is disinfected by the hydrogen peroxide silver ions, and thus the tap water can be directly added. During maintenance, the waste hydrogen peroxide silver ion liquid 45 in the instantaneous sterilization device 2 may be discharged through a waste liquid discharge port 36 arranged at a bottom portion of the instantaneous sterilization device 2.

In FIG. 3, the instantaneous sterilization device comprises an air inlet 1, a sterilized air outlet 3, a fan 13, a spray pump 7, a spray pipe 8, a nozzle 9 and a hydrogen peroxide silver ion liquid device 44, wherein a hydrogen peroxide silver ion liquid 45 and a hydrogen peroxide silver ion solution 47 are added in the hydrogen peroxide silver ion liquid device 44.

After the fan 13 works, the instantaneous sterilization device 2 forms a negative pressure, air contaminated by bacteria and viruses is sucked from the air inlet 1, the dense hydrogen peroxide silver ion spray liquid and the contaminated air forcedly sucked by the fan 13 reversely collide, rub and wash for disinfection. If the instantaneous sterilization device 2 has a certain vertical height or horizontal length, the disinfection time is prolonged, and the effect of killing bacteria and viruses is improved. The sterilized air is discharged through the sterilized air outlet 3. In order to prevent the hydrogen peroxide silver ion spray liquid from drifting out of the sterilized air outlet 3 and entering the air, the instantaneous sterilization device 2 is internally provided with an air-water separating device 37. The air-water separating device 37 is located above the nozzle 9 and below an air inlet end of the fan 13. The air-water separating device 37 blocks hydrogen peroxide silver ion fog drops and returns the fog drops to the sprayed hydrogen peroxide silver ion spray liquid 48, and the clean sterilized air is discharged to a required place.

Although the disinfection speed of the present application is not faster and more thorough than the disinfection speed equipped with the ULPA high efficiency particle air filter 11 or the HEPA high efficiency particle air filter 49 combined with the hydrogen peroxide silver ion, the present application is more suitable for large-volume ventilation occasions due to smaller wind resistance and lower fan electric power.

As shown in FIG. 4, the instantaneous sterilization device comprises the air inlet 1, the sterilized air outlet 3, the fan 13, a microporous air-liquid mixer 26 and a hydrogen peroxide silver ion liquid device 44, wherein a hydrogen peroxide silver ion liquid 45 and a hydrogen peroxide silver ion solution 47 are added in the instantaneous sterilization device 2.

The microporous air-liquid mixer 26 is immersed at a bottom portion of the hydrogen peroxide silver ion solution 47, an air inlet of the microporous air-liquid mixer 26 is connected with the air exhaust end of the fan 13 by an air pipe 17 through an air-liquid mixer interface 24, and the air inlet end of the fan 13 is communicated with contaminated air through the air inlet 1. After the fan 13 is running, air containing bacteria and viruses is sucked from the air inlet 1 and sent into the microporous air-liquid mixer 26, the air in the microporous air-liquid mixer 26 is cut into very fine air components, tiny bubbles are sprayed to the hydrogen peroxide silver ion solution 47 by the microporous air-liquid mixer 26, and the tiny bubbles float from bottom to top and move upwards in the hydrogen peroxide silver ion solution 47 due to the fact that the mass of the air is smaller than that of the liquid. In the process of drifting, the bacteria and the viruses in the air are killed by the hydrogen peroxide silver ion solution. The smaller the diameter of the bubbles, the higher the probability that the bacteria and viruses will come into contact with the hydrogen peroxide silver ion solution 47 respectively, and the better the friction disinfection effect. The sterilized air is discharged out of the instantaneous sterilization device 2 through the sterilized air outlet 3, thus completing the function of killing the virus particles.

A liquid level of the hydrogen peroxide silver ion solution 47 varies with a wind pressure of the fan 13, so that a certain distance height is kept between the liquid level and the sterilized air outlet 3 to prevent the hydrogen peroxide silver ion solution 47 from overflowing.

Figure 5:
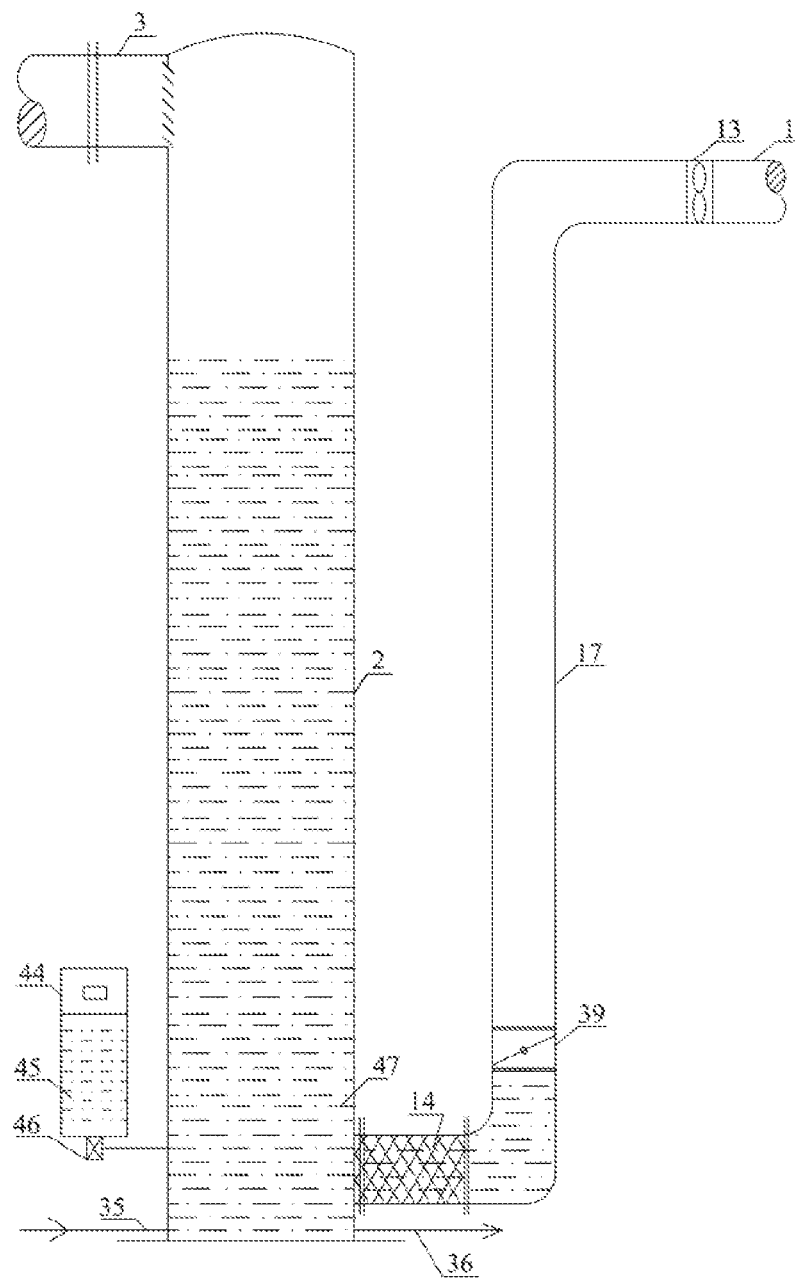
FIG. 5 is a schematic diagram of instantaneous sterilization through pipeline air-liquid mixing sterilization of hydrogen peroxide silver ions according to the instantaneous sterilization system for ventilation and air conditioning provided by the present application.

In FIG. 5, the instantaneous sterilization device 2 comprises the air inlet 1, the sterilized air outlet, the fan 13, a pipeline air-liquid mixer 14, and a hydrogen peroxide silver ion liquid device 44. A hydrogen peroxide silver ion liquid 45 and a hydrogen peroxide silver ion solution 47 are added in the instantaneous sterilization device 2.

Figure 4:
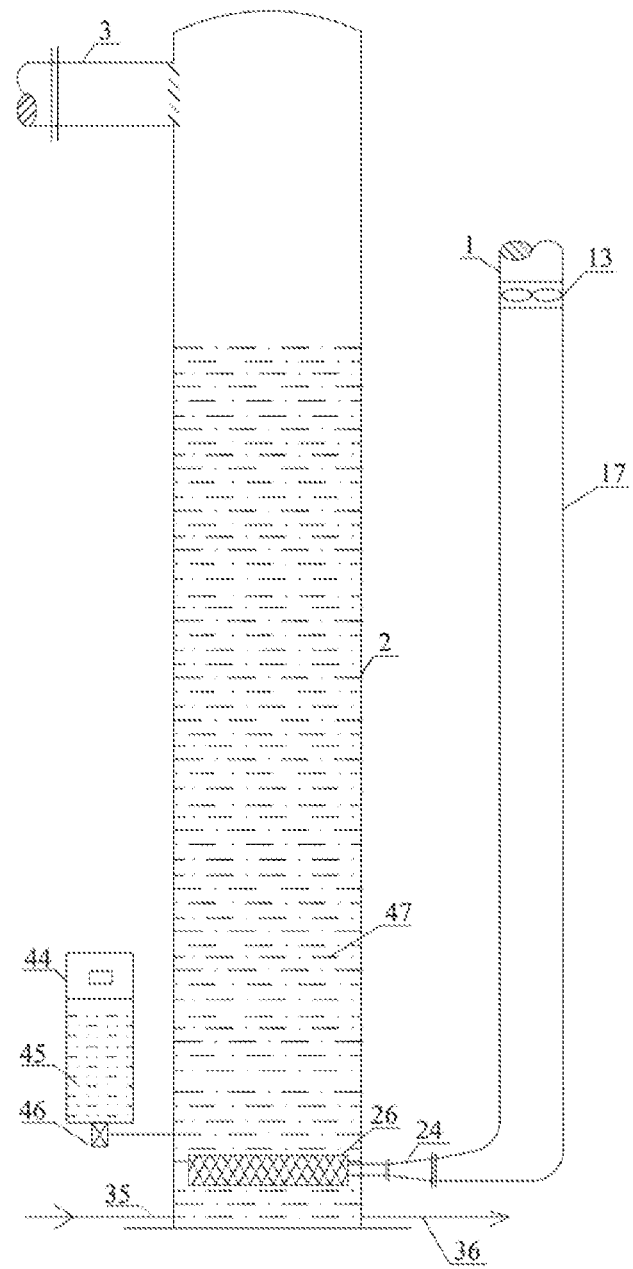
FIG. 4 is a schematic diagram of hydrogen peroxide silver ion disinfection through microporous air-liquid mixing according to the instantaneous sterilization system for ventilation and air conditioning provided by the present application.

The pipeline air-liquid mixer 14 has substantially the same function as the microporous air-liquid mixer 26 shown in FIG. 4, except that the hydrogen peroxide silver ion solution 47 is immersed in the pipeline air-liquid mixer 14, and the pipeline air-liquid mixer 14 is provided with an air cutting device capable of cutting air into fine air components. The air containing pollution is cut by the air cutting device and mixed with the hydrogen peroxide silver ion solution 47 in the pipeline air-liquid mixer 14 when passing through the pipeline air-liquid mixer 14, after mixing, the air is collided at high speed to move, and form tiny bubbles, the tiny bubbles and the solution are mixed into a gas-liquid mixture and rotate at a high speed. Finally, the gas-liquid mixture enters the hydrogen peroxide silver ion solution 47 through an outlet of the pipeline air-liquid mixer 14, and the tiny bubbles continuously drift upwards in the hydrogen peroxide silver ion solution 47 because the gas-liquid mixture is lighter than the liquid, the bacteria and viruses in the air are fully contacted, rubbed, washed and disinfected with the hydrogen peroxide silver ion solution 47 in the floating movement process, and the disinfection time is in direct proportion to the vertical height of the instantaneous sterilization device 2. The disinfected and sterilized air is discharged from the sterilized air outlet 3 to finish instantaneous sterilization.

Figure 6:
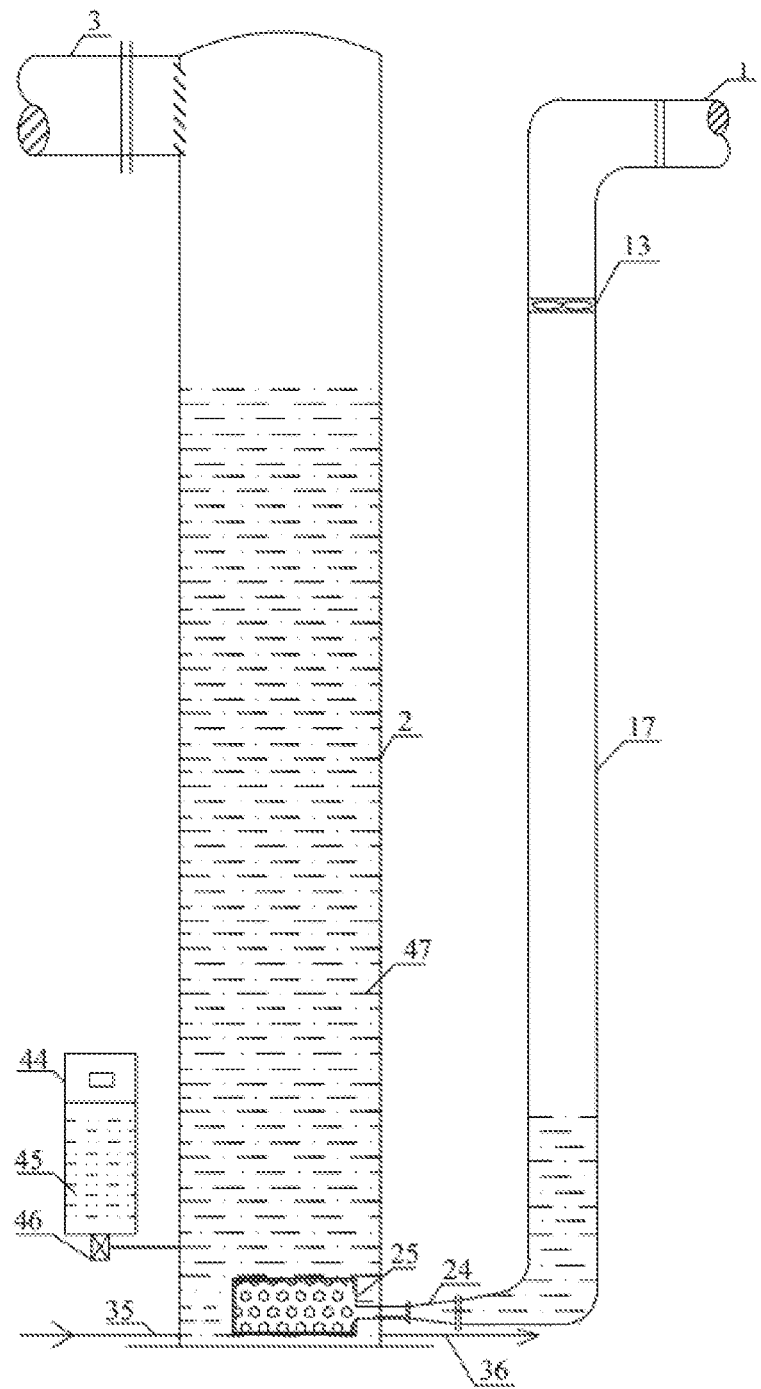
FIG. 6 is a schematic diagram of instantaneous sterilization through air-liquid mixing disinfection according to the instantaneous sterilization system for ventilation and air conditioning provided by the present application.

As shown in FIG. 6, the instantaneous sterilization device 2 comprises the air inlet 1, the sterilized air outlet 3, the fan 13, an immersion air-liquid mixer 25 and a hydrogen peroxide silver ion liquid device 44, wherein a hydrogen peroxide silver ion liquid 45 and a hydrogen peroxide silver ion solution 47 are added in the hydrogen peroxide silver ion liquid device 44.

FIG. 6, FIG. 4 and FIG. 5 belong to a gas-liquid mixed type disinfection process, the immersion air-liquid mixer 25 is immersed in the hydrogen peroxide silver ion solution 47 and configured at the bottom portion of the hydrogen peroxide silver ion solution 47, the contaminated air is injected into the immersion air-liquid mixer 25 by air bubbles through the air inlet 1 by the fan 13 at a high speed, and the air rotates at a high speed in the immersion air-liquid mixer 25 due to the structure. A liquid-gas mixture is sprayed to the hydrogen peroxide silver ion solution 47 and rotates in the hydrogen peroxide silver ion solution 47, so as to drive the surrounding hydrogen peroxide silver ion solution 47 to stir, so that the contaminated air is fully mixed with the hydrogen peroxide silver ion solution 47 for disinfection, and then enters the hydrogen peroxide silver ion solution 47 to float upwards and move and fully contact with the hydrogen peroxide silver ion solution 47 to achieve disinfection and sterilization.

Figure 7:
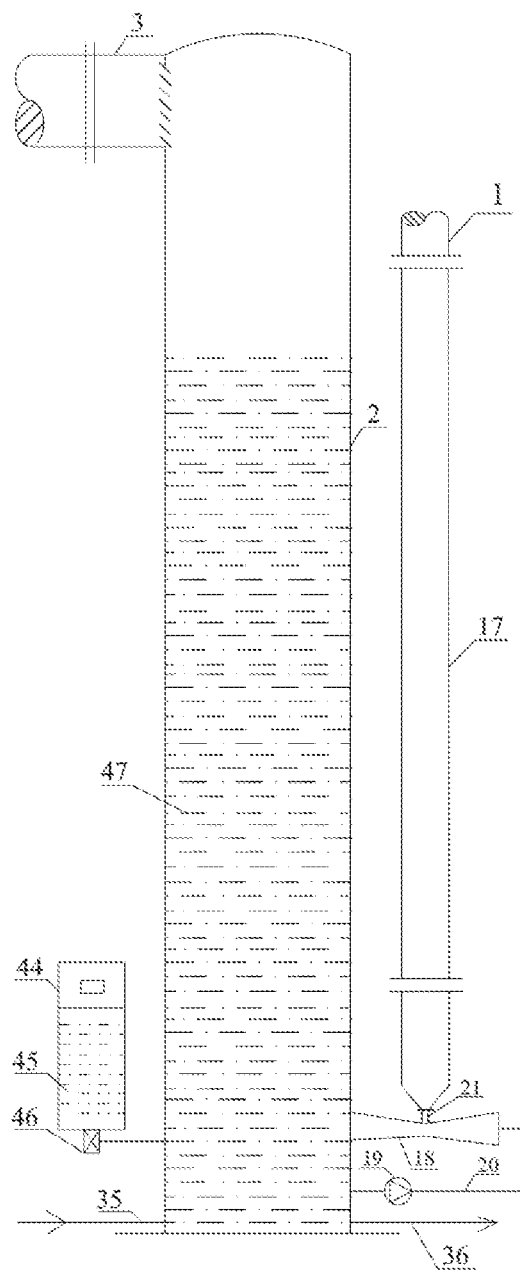
FIG. 7 is a schematic diagram of instantaneous sterilization through Venturi pipe air-liquid mixing disinfection according to the instantaneous sterilization system for ventilation and air conditioning provided by the present application.

In FIG. 7, the instantaneous sterilization device 2 comprises the air inlet 1, the sterilized air outlet 3, the fan 13, a Venturi air-liquid mixer 18, a Venturi circulating pump 19, a Venturi intakeport 21 and a hydrogen peroxide silver ion liquid device 44, wherein a hydrogen peroxide silver ion liquid 45 and a hydrogen peroxide silver ion solution 47 are added in the hydrogen peroxide silver ion liquid device 44.

The air inlet 1 is connected with the Venturi intakeport 21, an inlet of the Venturi air-liquid mixer 18 is connected with an output end of the Venturi circulating pump 19, an input end of the Venturi circulating pump 19 is connected with a lower portion of the instantaneous sterilization device 2 and is communicated with the hydrogen peroxide silver ion solution 47. In FIG. 7, the instantaneous sterilization device 2 realizes the mixing and disinfection of contaminated air and the hydrogen peroxide silver ion solution 47 through the Venturi air-liquid mixer by utilizing a Venturi principle. When running, the input end of the Venturi circulating pump 19 sucks in the hydrogen peroxide silver ion solution 47, then the hydrogen peroxide silver ion solution 47 is input into the inlet of the Venturi air-liquid mixer 18 by a Venturi pump circulating pipe 20, and flows into the hydrogen peroxide silver ion solution 47 of the Venturi air-liquid mixer 18 through the Venturi principle, which may lead to a vacuum negative pressure formed at the Venturi intakeport 21, then the air is sucked into the Venturi intakeport 21 through the air inlet 1, and a suction amount of the air is in a certain proportion to a flow of the Venturi pump circulating pipe 20. The air enters the Venturi air-liquid mixer 18. According to the Venturi principle, the contaminated air and the hydrogen peroxide silver ion solution 47 are fully mixed and exploded in the Venturi air-liquid mixer 18, a mixed air liquid formed by the contaminated air and the hydrogen peroxide silver ion solution 47 is sprayed to the hydrogen peroxide silver ion solution 47 by the Venturi air-liquid mixer 18 and drifts upwards in the hydrogen peroxide silver ion solution 47. Finally, the air sterilized by the hydrogen peroxide silver ion solution 47 is discharged from the sterilized air outlet 3, so that the instantaneous sterilization is completed. The venturi air-liquid mixer 18 in FIG. 7 has a good air-liquid mixing effect, and when the air is exploded in the Venturi air-liquid mixer 18, bacteria and viruses in the air are fully combined with the hydrogen peroxide silver ions for disinfection, so that the effect of disinfection by air-liquid mixing and contact of the bacteria and the viruses with the hydrogen peroxide silver ions is very ideal.

Figure 8:
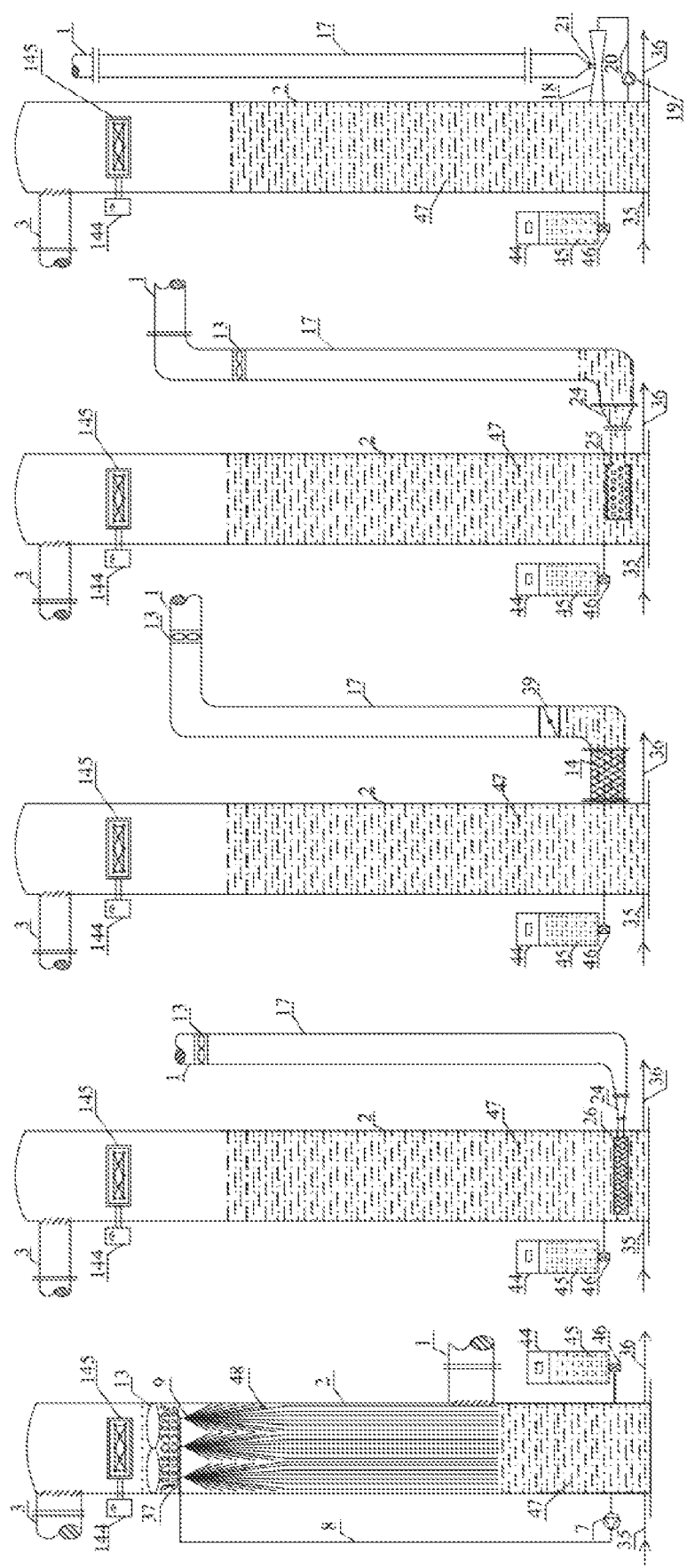
FIG. 8 is a schematic diagram of instantaneous sterilization through the combination of hydrogen peroxide silver ions and microwave, laser or infrared rays according to the instantaneous sterilization system for ventilation and air conditioning provided by the present application.

In FIG. 8, the instantaneous sterilization device 2 is simultaneously configured with a microwave disinfecting device 144 and a microwave generator 145, or simultaneously configured with a laser disinfecting device 146 and a laser generator 147, or simultaneously configured with an infrared disinfecting device 153 and an infrared generator 154 on the basis of FIG. 3, FIG. 4, FIG. 5, FIG. 6 and FIG. 7.

The microwave disinfecting device 144, the laser disinfecting device 146 or the infrared disinfecting device 153 is configured above a liquid level of the hydrogen peroxide silver ion solution 47 and below the sterilized air outlet 3, and the microwave disinfecting device 144, or the laser disinfecting device 146 or the infrared disinfecting device 153 in FIG. 8 belongs to a dry heat sterilization mode, and bacteria and viruses are killed by utilizing high temperature. An electronic oscillating circuit in the microwave disinfecting device 144 generates VHF electromagnetic waves, which resonate through a VHF resonant cavity of a magnetron to generate microwaves, and the microwaves are radiated by the microwave generator 145 to the contaminated air passing through a waveguide. The microwaves belong to direct waves, have extremely strong penetrating power, rapidly enable bacteria and virus spores to move back and forth according to a microwave frequency under the action of a microwave field, and the virus particles collide and rub with each other to generate high heat to achieve the effect of inactivating the bacteria and the viruses.

The laser disinfecting device 146 irradiates laser beams to the passing contaminated air through the laser generator 147. Selecting the laser with preset frequency will produce extremely high temperature for the bacteria and the viruses, quickly kill the bacteria and the viruses, and achieve instantaneous sterilization. Lasers with wavelengths between 25,000-28,000 nm have strong sterilizing power, and are most effective at 26,500 nm.

The infrared disinfecting device 153 generates infrared rays through the infrared generator 154, and sterilizes by using infrared radiation. The infrared ray is an electromagnetic wave using an electromagnetic wave frequency spectrum of 0.77-1,000 microns, has better heat effect, particularly has the strongest heat effect on the infrared ray with a frequency spectrum wavelength of 1-10 microns, and belongs to a dry heat sterilization technology with the two types above. The infrared ray is generated by an infrared ray bulb, which does not need air conduction, so that the heating speed is high. But the heat effect can only produce sterilization effect on bacteria and viruses which irradiate to the surface of the contaminated air.

The three dry heat sterilization configurations have ideal sterilization effect in a large-air-volume ventilation and air conditioning system. During running, firstly, the contaminated air is sucked in from the air inlet 1 through the fan 13, the air is disinfected through the hydrogen peroxide silver ion solution 47 in a spraying or air-liquid mixing mode, and then the disinfected air is used for killing the bacteria and the viruses through the microwave disinfecting device 144, or the laser disinfecting device 146 or the infrared disinfecting device 153, to achieve the instantaneous sterilization of the ventilation and air conditioning.

In one embodiment, the microwave disinfecting device 144, the laser disinfecting device 146 or the infrared disinfecting device 153 may also independently complete the instantaneous sterilization of the ventilation and air conditioning by the microwave disinfecting device 144, the laser disinfecting device 146 or the infrared disinfecting device 153 without performing the primary disinfection process of spraying the hydrogen peroxide silver ion solution 47 or the air-liquid mixing.

However, no matter the configuration of the microwave disinfecting device 144 and the microwave generator 145, or the configuration of the laser disinfecting device 146 and the laser generator, or the configuration of the infrared disinfecting device 153 and the infrared generator 154, which are applied to the sterilization system for ventilation and air conditioning, a dust problem is inevitable, and the ventilation system needs to be provided with a primary or medium-efficiency filter screen. However, the primary or medium-efficiency filter screen is often required to be manually replaced and cleaned, and it is still a dangerous job to replace the filter screen in places such as contagious wards where infectious bacteria and viruses are rampant. The process of disinfection with the hydrogen peroxide silver ion solution 47 through spraying or air-liquid mixing not only plays a role of disinfection, but also can achieve the function of primary or medium-efficiency filtration. Moreover, the dust is washed and then enters the hydrogen peroxide silver ion solution 47 for disinfection through spraying or air-liquid mixing. Because it is very easy and simple to replace the hydrogen peroxide silver ion liquid 45, the hydrogen peroxide silver ion solution 47 can be automatically replaced to realize unmanned intelligent operation.

Figure 9:
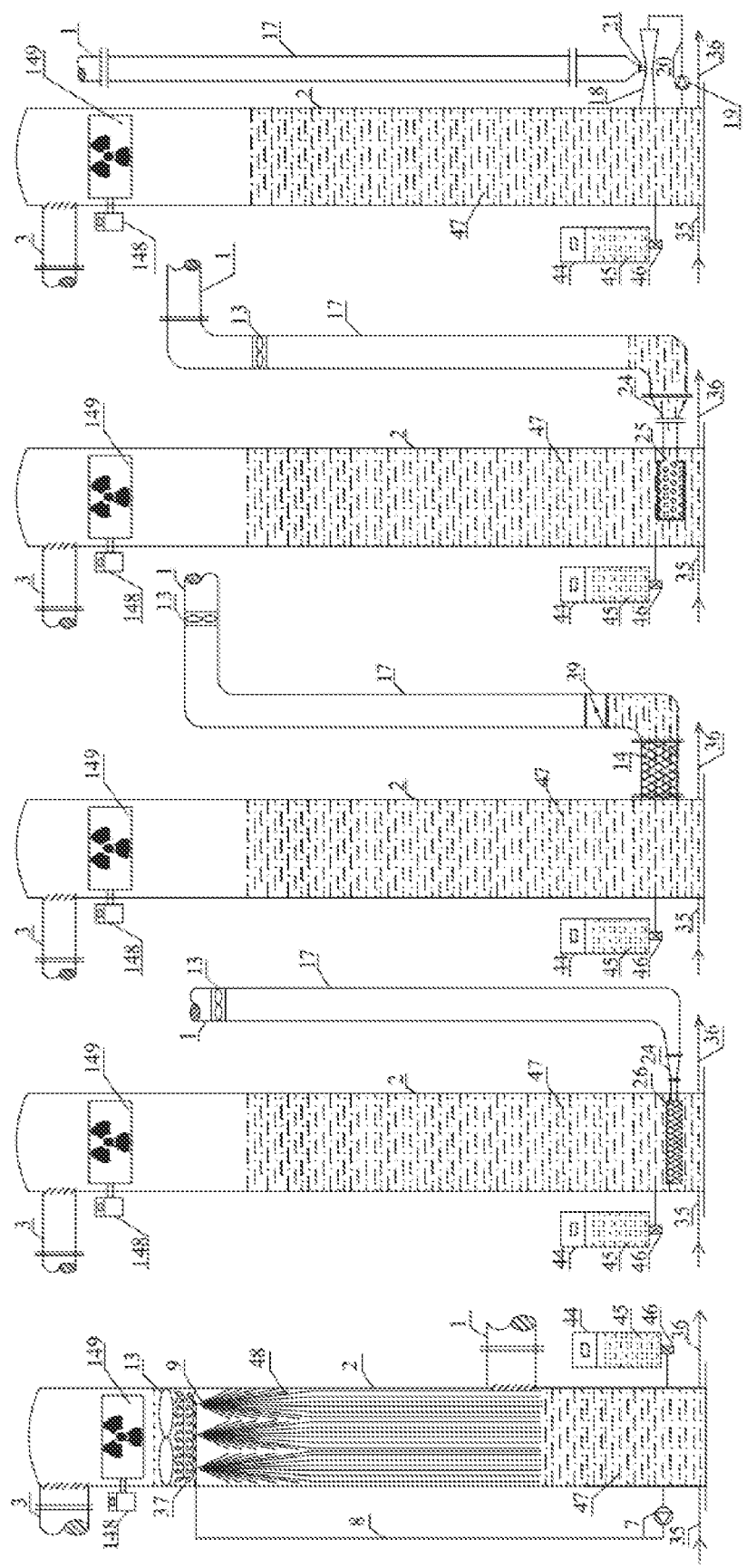
FIG. 9 is a schematic diagram of instantaneous sterilization through the combination of hydrogen peroxide silver ions and X-rays or γ-rays according to the instantaneous sterilization system for ventilation and air conditioning provided by the present application.

In FIG. 9, the instantaneous sterilization device 2 is simultaneously configured with an X-ray disinfecting device 148 and an X-ray generator 149, or simultaneously configured with a γ-ray disinfecting device 150 and a γ-ray generator 151 on the basis of FIG. 3, FIG. 4, FIG. 5, FIG. 6 and FIG. 7.

The X-ray generator 149 or the γ-ray generator 151 is configured above the liquid level of the hydrogen peroxide silver ion solution 47 and configured below the sterilized air outlet 3. The configuration of the X-ray disinfecting device 148 and the X-ray generator 149 or the configuration of the γ-ray disinfecting device 150 and the γ-ray generator in FIG. 9 belongs to ionizing radiation sterilization, which can kill the bacteria and the viruses.

The X-ray disinfecting device 148 may generate X-rays with tens of thousands of electron volts, and the transition of electrons from high energy levels to low energy levels may radiate photons. If there is a large difference in the energy level, photons in the X-ray band may be emitted.

The X-ray is an electromagnetic wave with extremely short wavelength and large energy, but the scientific community still has no conclusion about whether the X-ray belongs to an electromagnetic wave or corpuscular radiation. The wavelength of the X-rays is shorter than that of visible light, and the photon energy of the X-ray is several tens to hundreds of thousands times larger than that of the visible light. The X-ray has strong penetrating power, and the irradiated air can penetrate through a virus shell. After the virus absorbs the X-ray, the temperature inside the shell is rapidly heated up and the virus is destroyed, thus inactivating the virus spores.

The γ-ray is a ray with stronger penetrating power. The X-ray is generated by the transition or excitation of electrons outside a nucleus and originated from outside the nucleus. The γ-ray is a source of decay, fission, or the like of the nucleus, is originated from inside the atomic nucleus, and essentially belongs to the electromagnetic wave. The γ-ray is a ray with stronger penetrating power than the X-ray, has stronger destructive power on the virus particles, and is mostly used for treating tumors of human bodies at present. The basic chemical composition of the virus particle is nucleic acid and protein, and after the γ-ray penetrates the virus particle, ionization occurs, resulting in ion-eroded virus protein and enzyme, which are the main components of living virus and living cell tissues which, once damaged, can inactivate cells and achieve instantaneous sterilization.

During running, firstly, the contaminated air is sucked in from the air inlet 1 through the fan 13 into the hydrogen peroxide silver ion solution 47 through spraying or air-liquid mixing, the disinfected air is sterilized through the X-ray disinfecting device 148 or the γ-ray disinfecting device 150 to kill the bacteria and the viruses to achieve the instantaneous sterilization system for ventilation and air conditioning.

In one embodiment, the X-ray disinfecting device 148 and the X-ray generator 149 are simultaneously configured, or the γ-ray disinfecting device 150 and the γ-ray generator 151 are simultaneously configured, or the primary disinfection process of the hydrogen peroxide silver ion solution 47 through spraying or air-liquid mixing is not required to be carried out, and the instantaneous sterilization of the ventilation and air conditioning is independently completed by simultaneously configuring the X-ray disinfecting device 148 and the X-ray generator 149, or simultaneously configuring the γ-ray disinfecting device 150 and the γ-ray generator 151.

However, whether the X-ray disinfecting device 148 and the X-ray generator 149 or the γ-ray disinfecting device 150 and the γ-ray generator 151 are simultaneously configured, the dust problem is inevitable, and the ventilation system needs to be configured with a primary or medium-efficiency filter screen. However, the primary or medium-efficiency filter screen often needs to be replaced and cleaned, and it is still a dangerous job to replace the filter screen in places such as contagious wards where infectious bacteria and viruses are rampant. The process of disinfection with the hydrogen peroxide silver ion solution 47 through spraying or air-liquid mixing not only plays a role of disinfection, but also can achieve the function of primary or medium-efficiency filtration. Moreover, the dust is washed and then enters the hydrogen peroxide silver ion solution 47 for disinfection through spraying or air-liquid mixing, and the hydrogen peroxide silver ion solution 47 can be automatically replaced to realize unmanned intelligent operation.

Figure 10:
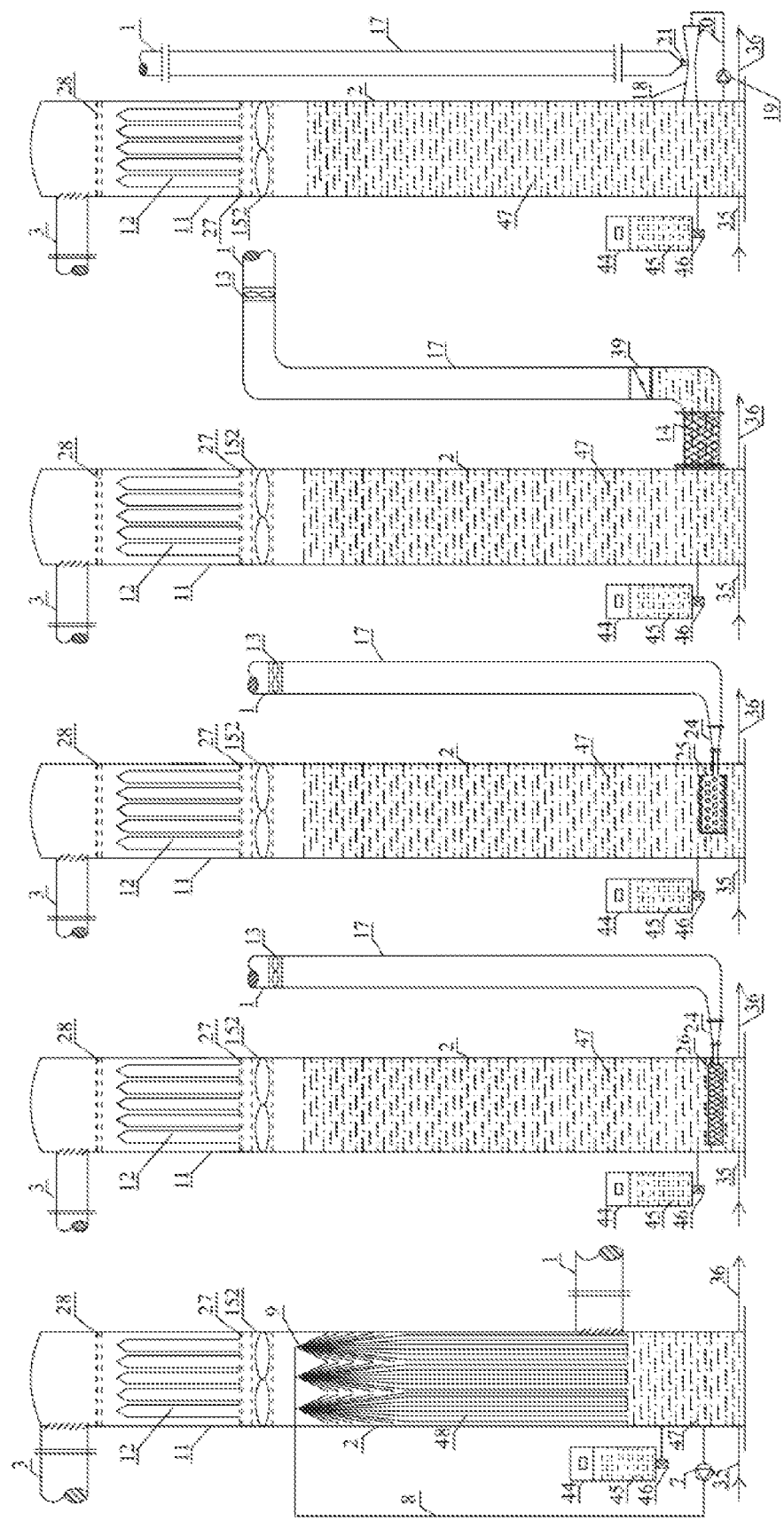
FIG. 10 is a schematic diagram of instantaneous sterilization through the combination of hydrogen peroxide silver ions and the ULPA ultra-efficient air filter or the HEPA high efficiency particle air filter according to the instantaneous sterilization system for ventilation and air conditioning provided by the present application.

In FIG. 10, the instantaneous sterilization device 2 is a combined instantaneous sterilization device for ventilation and air conditioning configured with one of the ULPA ultra-efficient air filter 11 or the HEPA high efficiency particle air filter 49, and a booster fan 152 on the basis of FIG. 3, FIG. 4, FIG. 5, FIG. 6 and FIG. 7.

The ULPA ultra-efficient air filter 11 or the HEPA high efficiency particle air filter 49 is configured above the booster fan 152 and is located between the booster fan 152 and the sterilized air outlet 3, the booster fan 152 is configured between the liquid level of the hydrogen peroxide silver ion solution 47 and the air inlet 27 of the HEPA filter or the air inlet 51 of the HEPA filter, the air inlet 27 of the HEPA filter or the air inlet 51 of the HEPA filter is connected with an air exhaust end of the booster fan 152, and the air outlet 28 of the ULPA ultra-efficient air filter or the air outlet 52 of the HEPA filter is connected with the sterilized air outlet 3.

Figure 3:
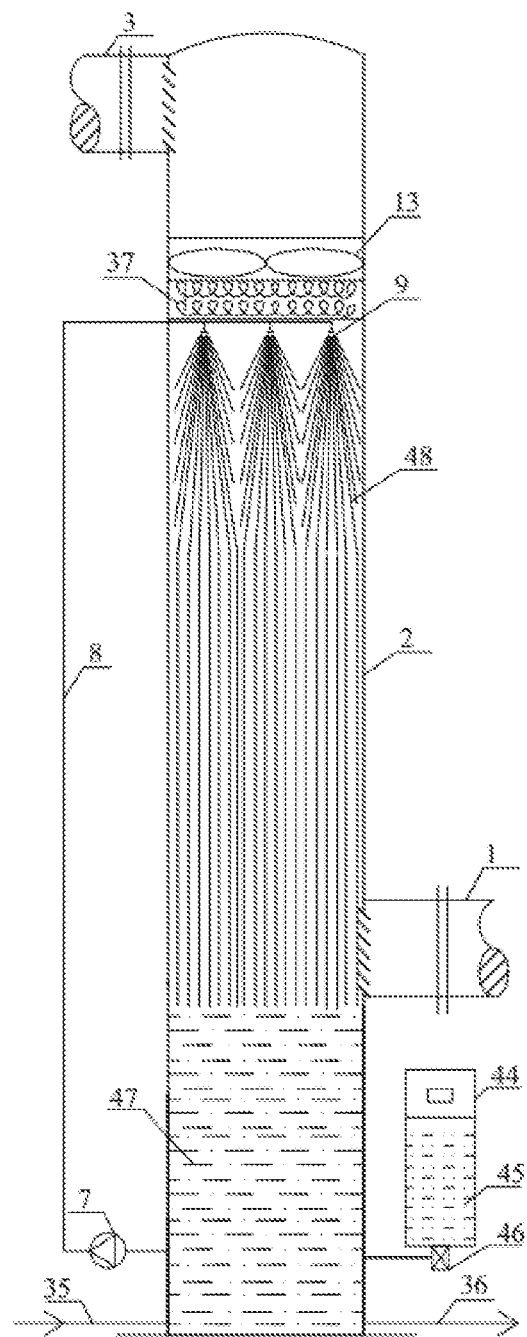
FIG. 3 is a schematic diagram of spray disinfection of hydrogen peroxide silver ions according to the instantaneous sterilization system for ventilation and air conditioning provided by the present application.

In FIG. 10, one of the ULPA ultra-efficient air filter 11 or the HEPA high efficiency particle air filter 49 is configured on the basis of FIG. 3, FIG. 4, FIG. 5, FIG. 6 and FIG. 7, which aims at achieving the instantaneous sterilization function. In FIG. 3, the contaminated air is disinfected by washing through the spray liquid, while in FIG. 4, FIG. 5, FIG. 6 and FIG. 7, the contaminated air is disinfected by the method of air-liquid mixing between the contaminated air and the hydrogen peroxide silver ion solution 47. Although the hydrogen peroxide silver ion solution 47 has very excellent sterilization ability, a dosage of the hydrogen peroxide silver ion solution cannot be increased at will. A standard dosage of the hydrogen peroxide silver ion solution 47 is about 1-3%. If the dosage is too large, the hydrogen peroxide silver ions will do harm to human respiratory tracts. Therefore, the object of instantaneous sterilization cannot be realized by normal proportioning dosage, so that the ULPA ultra-efficient air filter 11 or the HEPA high efficiency particle air filter 49 is configured on the basis of the hydrogen peroxide silver ion sterilization in this embodiment, that is, the ULPA ultra-efficient air filter 11 or the HEPA high efficiency particle air filter 49 can block the bacteria and viruses instantaneously, and then the hydrogen peroxide silver ions are used for sterilization, so that the instantaneous sterilization of the ventilation and air conditioning is finally realized.

Figure 11:
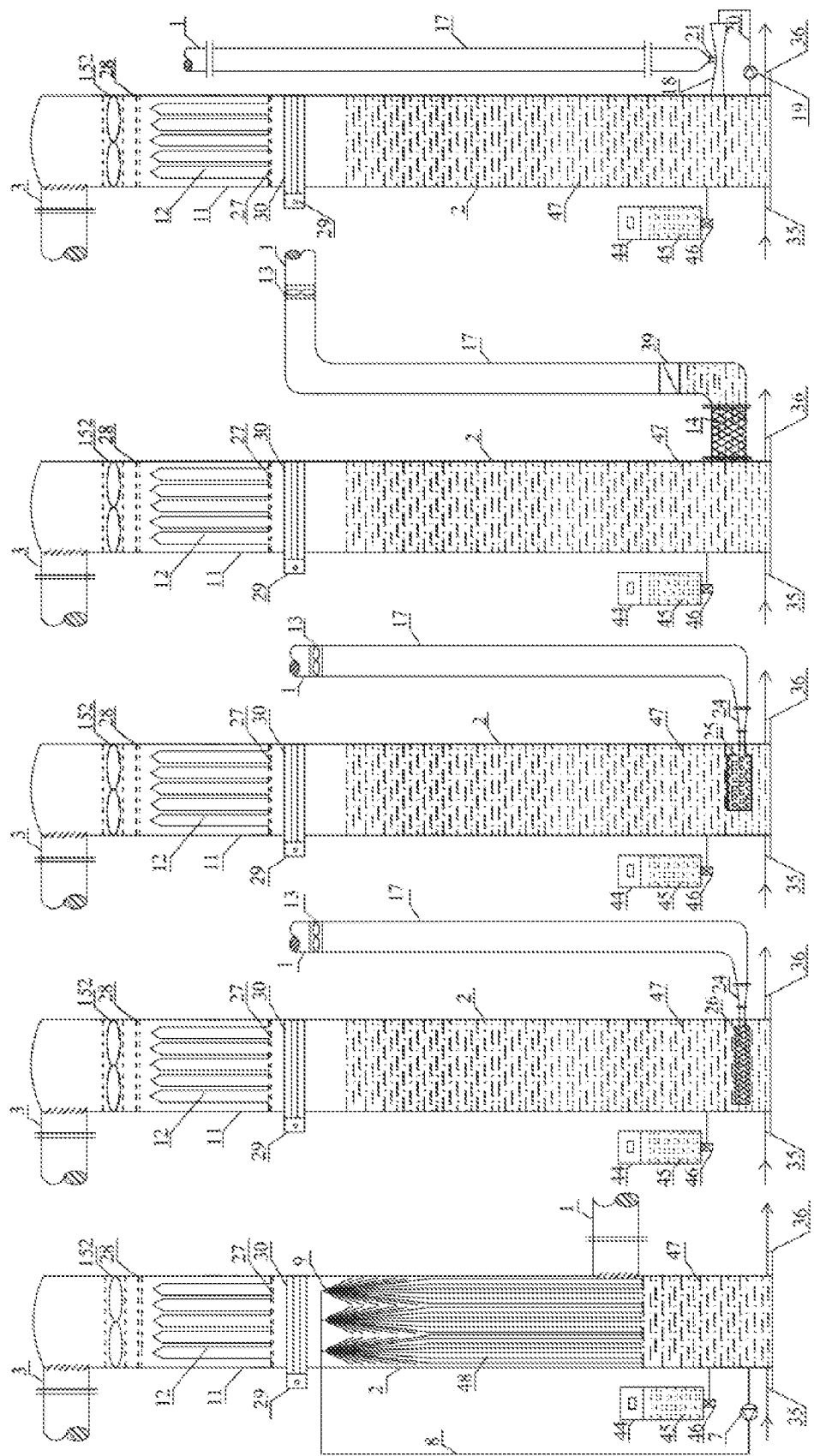
FIG. 11 is a schematic diagram of instantaneous sterilization through the combination of hydrogen peroxide silver ions, the ULPA ultra-efficient air filter or the HEPA high efficiency particle air filter and ultraviolet rays according to the instantaneous sterilization system for ventilation and air conditioning provided by the present application.

In FIG. 11, the instantaneous sterilization device 2 is provided with an ultraviolet disinfecting device 29 and an ultraviolet lamp tube 30 on the basis of FIG. 10.

The ultraviolet lamp tube 30 is configured between the liquid level of the hydrogen peroxide silver ion solution 47 and the air inlet 27 of the HEPA filter or the air inlet 51 of the HEPA filter, the booster fan 152 is configured between the sterilized air outlet 3 and the air outlet 28 of the ULPA ultra-efficient air filter, or between the sterilized air outlet 3 and the air outlet 52 of the HEPA filter, and an air exhaust end of the booster fan 152 is connected with the sterilized air outlet 3. The function of the booster fan 152 is the same as that of the position installed in FIG. 10. However, the object of FIG. 11 is to adjust the booster fan 30 above the filter without affecting the direct irradiation of bacteria and viruses in the air inlet 27 of the HEPA filter or the air inlet 51 of the HEPA filter by the ultraviolet lamp tube 30.

The ultraviolet disinfecting device 29 generates ultraviolet ray light through the ultraviolet lamp tube 30, and this embodiment is a method for sterilizing the bacteria and the viruses by irradiating the contaminated air with ultraviolet rays. Ultraviolet rays are directly irradiated to a surface of an object, air and water to sterilize, and cannot sterilize by diffraction, so that a back of the object cannot be sterilized in places where the ultraviolet rays cannot be irradiated. Generally, ultraviolet rays with a wavelength of 200-300 nm are used for sterilization, and the sterilization effect is the strongest especially at the wavelength is 253.7 nm. The absorption of the virus cell to the light wave is maximum at the positions of 250-270 nm, and the virus is irradiated by ultraviolet rays to destroy the nucleic acid of the virus, so that the nucleic acid structure is mutated, the virus cell body is dead or loses the reproductive capacity, so as to achieve the object of sterilization. Therefore, directly irradiating the air inlet 27 of the HEPA filter or the air inlet 51 of the HEPA filter with the ultraviolet lamp tube 30 means directly irradiating ultraviolet rays to kill and block the bacteria and the viruses that block accumulated on the ULPA ultra-efficient filter element 12 or the HEPA filter element screen 50, thus achieving instantaneous sterilization.

The ultraviolet disinfection lamp is divided into an ozone type and an ozone-free type, if the ultraviolet disinfection lamp is independently applied to an indoor disinfection occasion, the ultraviolet disinfection lamp is generally used for disinfection under an indoor unmanned condition, and the ozone type ultraviolet disinfection lamp may be adopted, because there is nobody indoors even if the ozone is harmful to the human bodies. Therefore, the ozone function can be enabled to improve the sterilization effect. However, the ozone may also be used for sterilization when there is nobody in the ventilation and air conditioning system. However, when there are people, it is not allowed to start the ozone operation because ozone is blown out to any corner of the air along with a ventilation and air conditioning pipeline system, which is harmful to people. Therefore, if there are people in the ventilation and air-conditioning system, the ozone ultraviolet disinfecting device cannot be used as the ventilation and air conditioning system is shared by disinfection and people.

Figure 12:
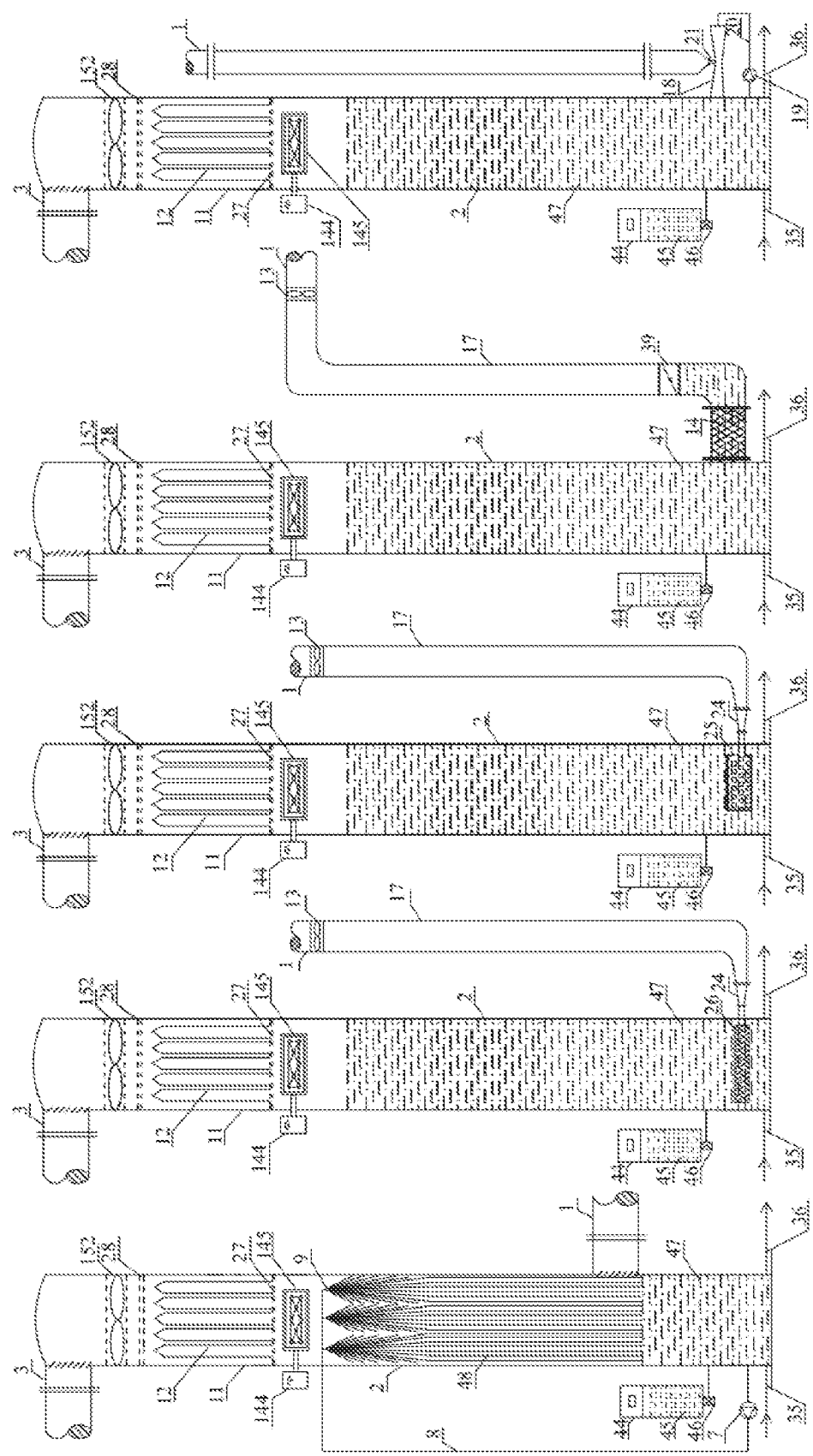
FIG. 12 is a schematic diagram of instantaneous sterilization through the combination of hydrogen peroxide silver ions, the ULPA ultra-efficient air filter or the HEPA high efficiency particle air filter and microwave or laser or infrared rays according to the instantaneous sterilization system for ventilation and air conditioning provided by the present application.

In FIG. 12, the instantaneous sterilization device 2 is a combined ventilation and air conditioning instantaneous disinfecting device which is provided with one of the ULPA ultra-efficient air filter 11 or the HEPA high efficiency particle air filter 49 and a booster fan 152 on the basis of FIG. 8.

The ULPA ultra-efficient air filter is configured above the microwave generator 145, the laser generator 147 or the infrared generator 154 and is located below the booster fan 152, or the HEPA high efficiency particle air filter is configured above the microwave generator 145, the laser generator 147 or the infrared generator 154 and is located below the booster fan 152, and the air inlet 27 of the HEPA filter is connected with one of the microwave generator 145, the laser generator 147 and the infrared generator 154, or the air inlet 51 of the HEPA filter is connected with one of the microwave generator 145, the laser generator 147 and the infrared generator 154. The air outlet 28 of the ULPA ultra-efficient air filter is connected with an air inlet end of the booster fan 152, or the air outlet (52) of the HEPA high efficiency particle air filter is connected with an air inlet end of the booster fan 152, the booster fan 152 is configured between the ULPA ultra-efficient air filter and the sterilized air outlet 3, or configured between the HEPA high efficiency particle air filter 49 and the sterilized air outlet 3, and the air outlet end of the booster fan 152 is connected with the sterilized air outlet 3.

This embodiment is configured with the booster fan 152 and one of the ULPA ultra-efficient air filter 11 or the HEPA high efficiency particle air filter 49 on the basis of FIG. 8, which is intended to improve a sterilization speed and achieve faster instantaneous sterilization efficiency of ventilation and air conditioning.

Figure 13:
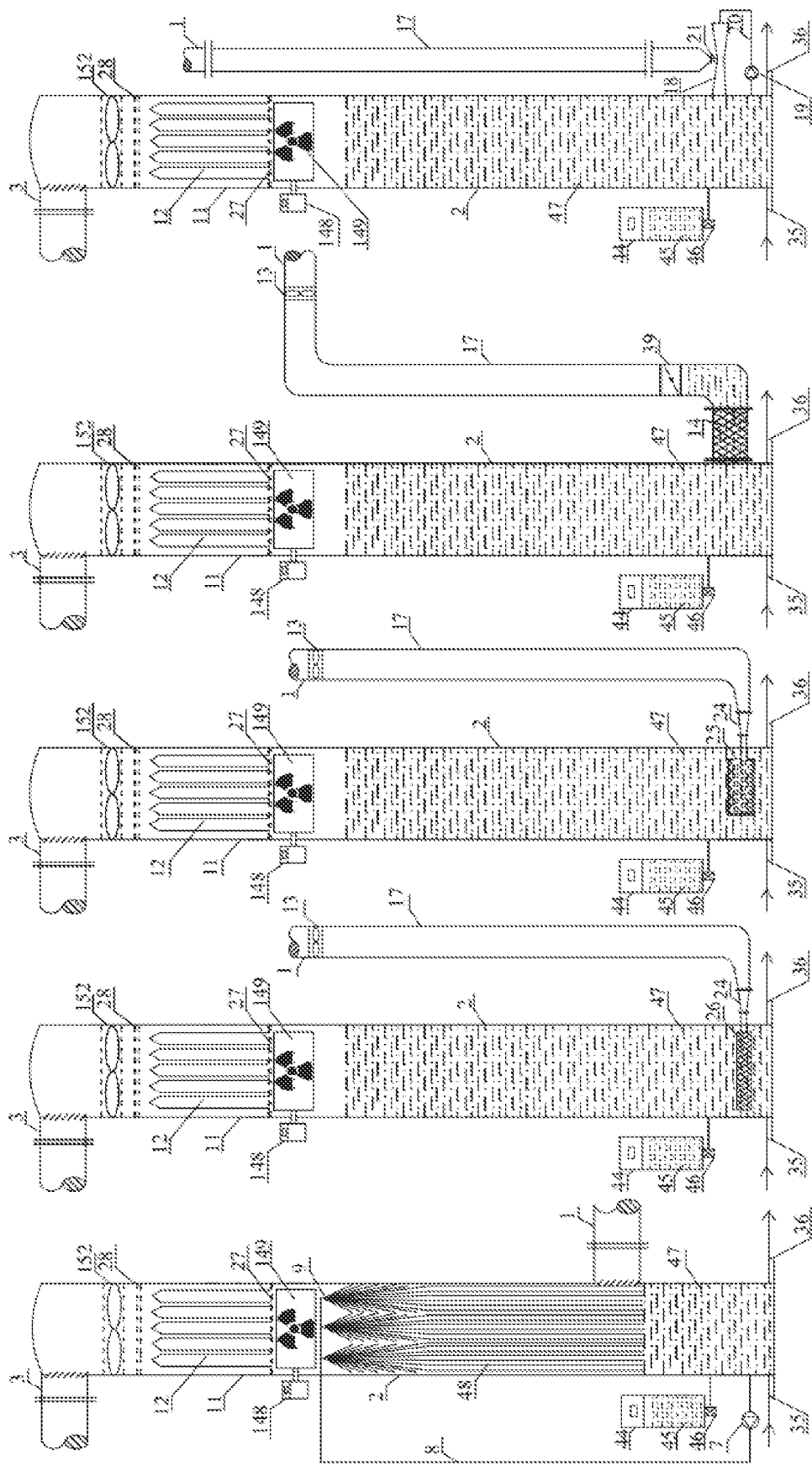
FIG. 13 is a schematic diagram of instantaneous sterilization through the combination of hydrogen peroxide silver ions, the ULPA ultra-efficient air filter or the HEPA high efficiency particle air filter and X-rays or γ-rays according to the instantaneous sterilization system for ventilation and air conditioning provided by the present application.

In FIG. 13, the instantaneous sterilization device 2 is provided with one of the ULPA ultra-efficient air filter 11 or the HEPA high efficiency particle air filter 49 and a booster fan 152 on the basis of FIG. 9.

The ULPA ultra-efficient air filter 11 or the HEPA high efficiency particle air filter 49 is configured between the X-ray generator 149 and the booster fan 152, or between the γ-ray generator 151 and the booster fan 152. The air inlet 27 of the HEPA filter is connected with one of the X-ray generator 149 and the γ-ray generator 151, the air inlet 51 of the HEPA filter is connected with one of the X-ray generator 149 and the γ-ray generator 151, the booster fan 152 is configured between the ULPA ultra-efficient air filter 11 and the sterilized air outlet 3, or configured between the HEPA high efficiency particle air filter 49 and the sterilized air outlet 3, and an air outlet end of the booster fan 152 is connected with the sterilized air outlet 3.

Figure 14:
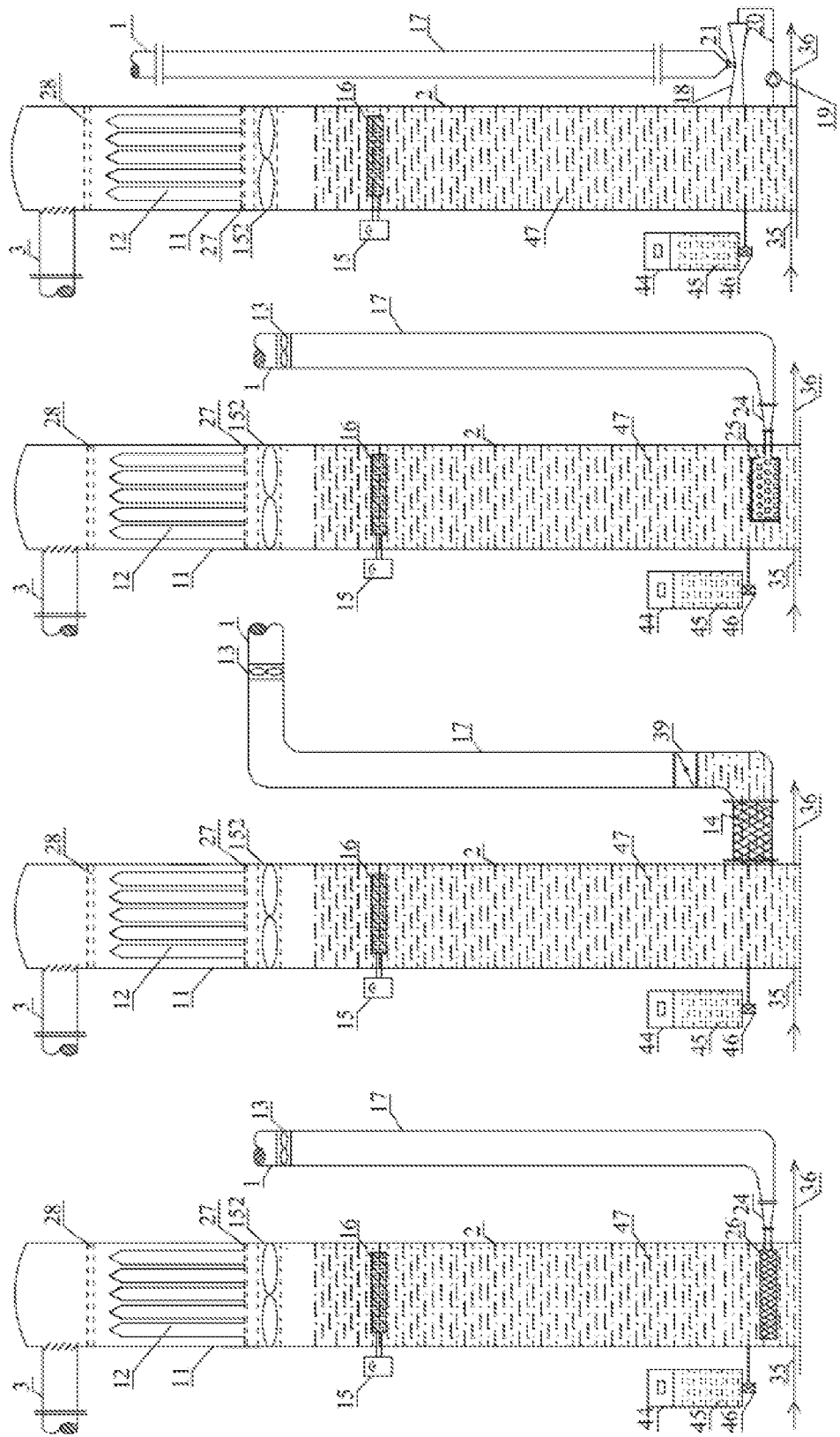
FIG. 14 is a schematic diagram of instantaneous sterilization through hydrogen peroxide silver ions configured with an ultrasonic spray liquid and the ULPA ultra-efficient air filter or the HEPA high efficiency particle air filter according to the instantaneous sterilization system for ventilation and air conditioning provided by the present application.

FIG. 14 is configured with an ultrasonic generator 16, a booster fan 152 and one of the ULPA ultra-efficient air filter 11 or the HEPA high efficiency particle air filter 49 on the basis of FIG. 4, FIG. 5, FIG. 6 and FIG. 7.

The ULPA ultra-efficient air filter 11 or the HEPA high efficiency particle air filter 49 is configured above the booster fan 152, and located between the booster fan 152 and the sterilized air outlet 3, and the air inlet 27 of the HEPA filter or the air inlet 51 of the HEPA filter is connected with an air exhaust end of the booster fan 152, and the booster fan 152 is configured above the liquid level of the hydrogen peroxide silver ion solution 47. The ultrasonic generator 16 is immersed in the hydrogen peroxide silver ion solution 47 and configured at an upper portion of the hydrogen peroxide silver ion solution 47. The ultrasonic generator 16 is connected with the ultrasonic atomizer 15.

In this embodiment, an electronic loop of the ultrasonic atomizer 15 generates high-frequency electronic oscillation, and the ultrasonic generator 16 generates high-frequency resonance in the liquid of the hydrogen peroxide silver ion solution 47. The high-frequency resonance of the ultrasonic generator 16 atomizes the liquid of the hydrogen peroxide silver ion solution 47 into fine liquid particles and throws the fine liquid particles off the liquid level of the hydrogen peroxide silver ion solution 47. The liquid fog particles of the hydrogen peroxide silver ion solution 47 exhausted by the booster fan 152 float on the ULPA ultra-efficient filter element 12 or the HEPA high efficiency filter element screen 50 along with the airflow to kill the bacteria and the viruses, prevent the propagation of the bacteria and the viruses, and achieve the object of instantaneous sterilization of the ventilation and air conditioning.

Figure 15:
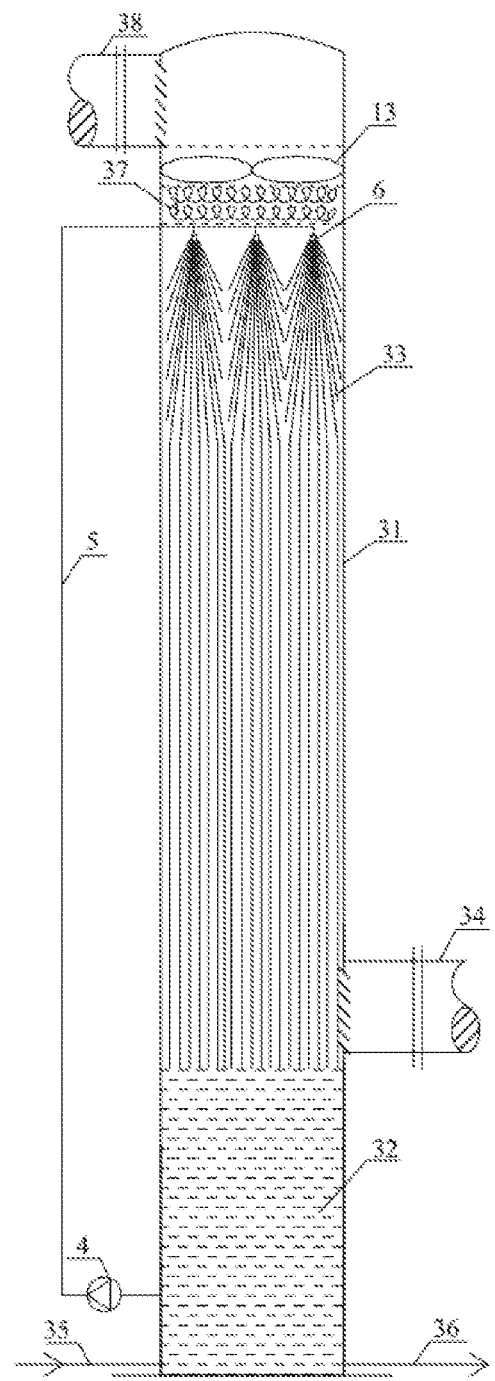
FIG. 15 is a schematic diagram of a device for water washing, spraying, filtering and deodorizing provided by the present application.

FIG. 15 is provided with a water-washing type spray device 31 comprising a clean water spray pump 4, a water-washing nozzle 6, a clean-water spray air inlet 34, an air-water separating device 37 and a clean-water spray air outlet 38.

Clean water 32 is configured in the water-washing type spray device 31, an input end of the clean water spray pump 4 is communicated with the clean water 32, an output end of the clean water spray pump 4 is connected with the water-washing nozzle 6 and sprays a clean water spray liquid 33, and the clean water spray air inlet 34 is communicated with the sterilized air outlet 3 of the instantaneous sterilization device 2 according to any one of FIG. 2 to FIG. 14.

To achieve instantaneous sterilization, it is often necessary to increase a concentration of the hydrogen peroxide silver ion solution 47 in the instantaneous sterilization device 2, which exceeds the standard allowed by human body. In order to prevent the concentration of the hydrogen peroxide silver ion solution 47 discharged from the over-standard sterilization air outlet 3 from drifting into the air and causing harm to the human body, the sterilized air outlet 3 of the instantaneous sterilization device 2 is further configured with one water-washing type spray device 31, so that the over-standard hydrogen peroxide silver ion solution 47 discharged from the sterilized air outlet 3 is forcely sucked in the clean-water spray air inlet 34 through the running fan 13 of the water-washing type spray device 31. The water-washing nozzle 6 sprays the clean water spray liquid 33 to wash reversely, and the floated over-standard hydrogen peroxide silver ion solution 47 collides with the sprayed clean water spray liquid 33 and falls into the clean water after washing. Because the hydrogen peroxide silver ions are easily soluble in water, a large amount of hydrogen peroxide silver ions are dissolved in the clean water, which eliminates peculiar smell and discharges the qualified sterilized air through the clean-water spray air outlet 38. Therefore, the dosage of the hydrogen peroxide silver ions can be increased by configuring one water-washing type spray device 31 at the output end of any instantaneous sterilization device 2 through the sterilized air outlet 3, which achieves the instantaneous sterilization speed and causes no affect to people.

The water-washing type spray device 31 is internally provided with the air-water separating device 37 to prevent the water fog drops in the spray liquid from drifting out of the clean-water spray air outlet 38 and entering the air to affect the surrounding environment. When the water fog drops drift to the air-water separating device 37, the air-water separating device 37 blocks the water fog drops and returns the water fog drops to the spray water fog, to achieve the effect of removing the water fog drops in the spray liquid.

Figure 16:
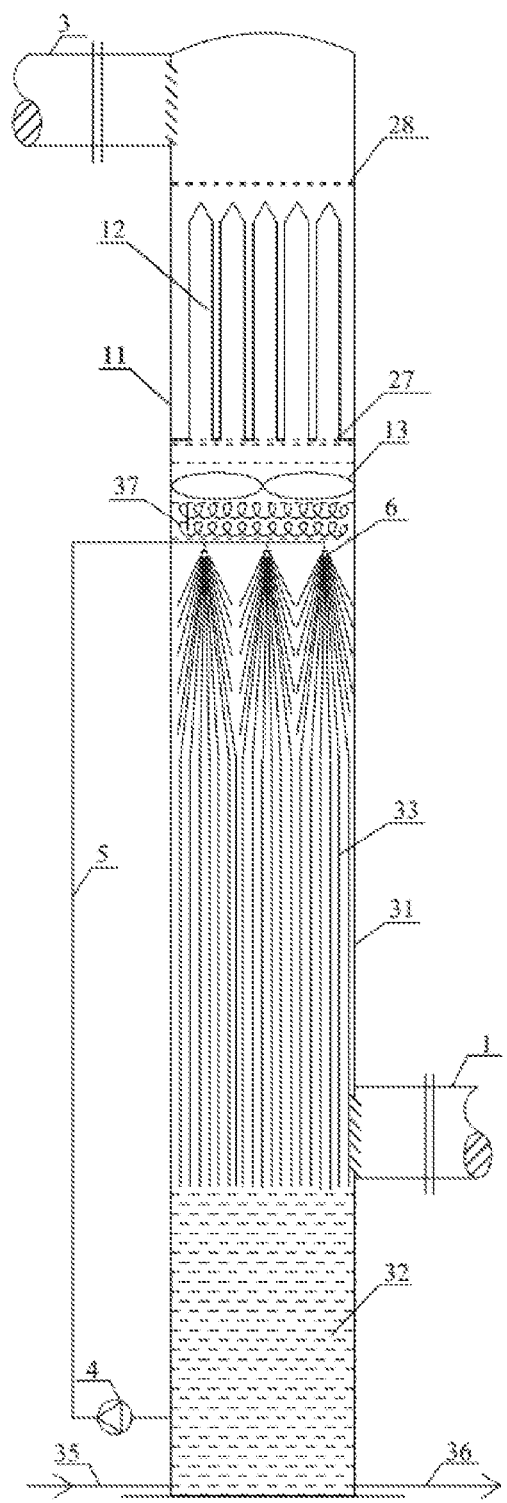
FIG. 16 is a schematic diagram of instantaneous sterilization through the combination of water-washing, spraying and filtering, and the ULPA ultra-efficient air filter or the HEPA high efficiency particle air filter according to the instantaneous sterilization system for ventilation and air conditioning provided by the present application.

In FIG. 16, the water-washing type spray device 31 is one of the ULPA ultra-efficient air filter 11 or the HEPA high efficiency particle air filter 49 on the basis of FIG. 15.

The ULPA ultra-efficient air filter 11 or the HEPA high efficiency particle air filter 49 is configured above the fan 13 and is located between the fan 13 and the sterilized air outlet 3, the air inlet 27 of the HEPA filter or the air inlet 51 of the HEPA filter is connected with the air exhaust end of the fan 13, and the air inlet end of the fan 13 is connected with the water-washing nozzle 6.

In this embodiment, the ULPA ultra-efficient air filter 11 or the HEPA high efficiency particle air filter 49 is configured on the basis of the water-washing type spray device 31, so that a simple and cheap instantaneous sterilization device for ventilation and air conditioning is formed, which especially has a certain application range in places with low sterilization requirement, for example, applied to a household primary air system, so as to realize a cheap primary air system for sterilization. The configuration of the ULPA ultra-efficient air filter 11 or the HEPA high efficiency particle air filter 49 on the water-washing type spray device 31 is to instantaneously block the bacteria and the viruses by using the ULPA ultra-efficient air filter 11 or the HEPA high efficiency particle air filter 49, and in turn, the water-washing type spray device 31 is used as the primary and medium-efficiency filters. Because the ULPA ultra-efficient filter element 12 of the ULPA ultra-efficient air filter 11 or the HEPA high efficiency filter element screen 50 of the HEPA high efficiency particle air filter 49 is expensive, in conventional application, both the ULPA ultra-efficient air filter 11 and the HEPA high efficiency particle air filter 49 should be equipped with the primary and medium-efficiency filters in front which filter out the dust and larger particles in the air before entering the ULPA ultra-efficient filter element 12 or the HEPA high efficiency filter element screen 50, then tiny particles are filtered out in the ULPA ultra-efficient filter element 12 or the HEPA high efficiency filter element screen 50, so as to prolong the service life of the ULPA ultra-efficient air filter 11 or the HEPA high efficiency particle air filter 49, and achieve the object of saving the replacement of the ULPA ultra-efficient air filter 11 or the HEPA high efficiency particle air filter 49.

As mentioned earlier, the primary and medium-efficiency filters need to be cleaned and replaced frequently, there is no problem in manually replacing the primary and medium-efficiency filters when there is no bacterial or viral infection in normal places. However, when an epidemic situation of infectious diseases is serious, or the filters are used in the environment of contagious wards where viruses are raging, it is appreciable that it is a very dangerous thing and job to manually clean and replace the primary and medium-efficiency filters. Therefore, using clean water to spray instead of the primary and medium-efficiency filters can not only play a role of filters, but the key point is that after the spray water of the water-washing spray device 31 is contaminated to a certain extent, it is very easy to automatically change sewage and add tap water, and all these can be easily cleaned and replaced automatically by no one, which is of great significance to the prevention and control of virus infection.

Figure 17:
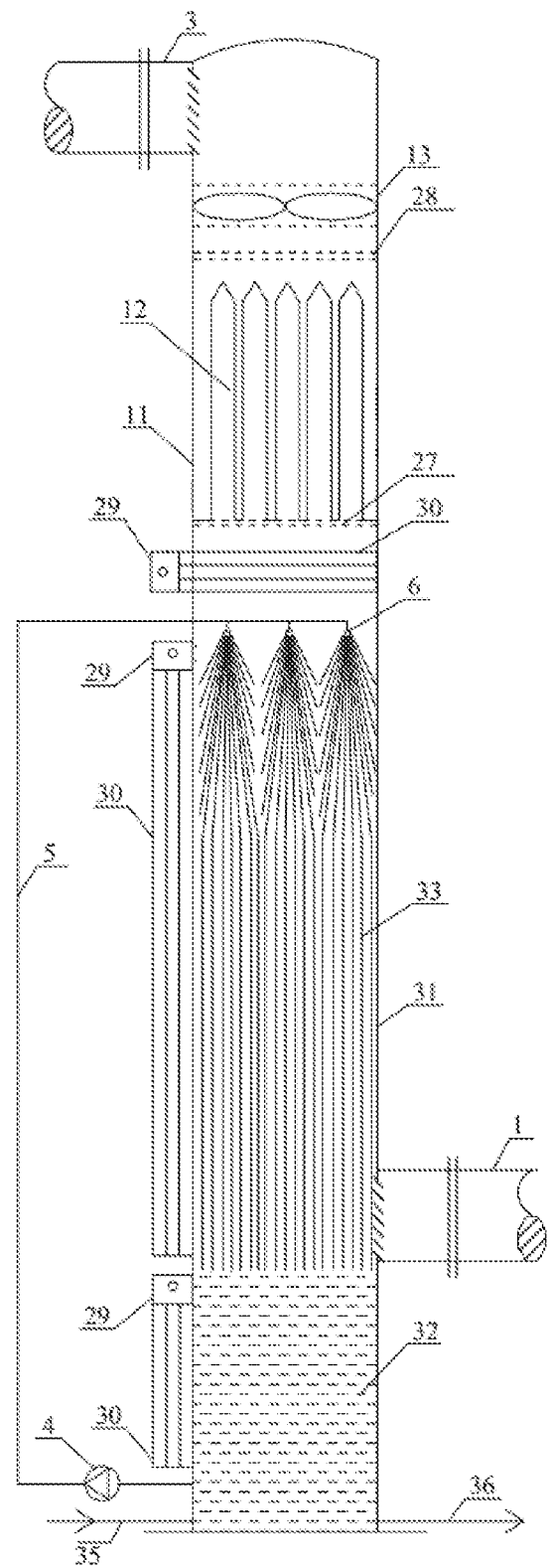
FIG. 17 is a schematic diagram of instantaneous sterilization through the combination of water-washing, spraying and filtering, and the ULPA ultra-efficient air filter or the HEPA high efficiency particle air filter combined with ultraviolet ray disinfection according to the instantaneous sterilization system for ventilation and air conditioning provided by the present application.

FIG. 17 is configured with an ultraviolet disinfecting device 29 and an ultraviolet lamp tube 30 on the basis of FIG. 16, wherein the ultraviolet disinfecting device 29 comprises a first ultraviolet disinfecting device, a second ultraviolet disinfecting device and a third ultraviolet disinfecting device, and the ultraviolet lamp tube 30 comprises a first ultraviolet lamp tube, a second ultraviolet lamp tube and a third ultraviolet lamp tube.

The first ultraviolet disinfecting device, the second ultraviolet disinfecting device and the third ultraviolet disinfecting device are respectively corresponding to the first ultraviolet lamp tube, the second ultraviolet lamp tube and the third ultraviolet lamp tube, and connected. The ULPA ultra-efficient air filter 11 or the HEPA high efficiency particle air filter 49 is configured between the first ultraviolet lamp tube 30 and the fan 13, the first ultraviolet lamp tube 30 is configured between the water-washing nozzle 6 and the air inlet 27 of the HEPA filter or the air inlet 51 of the HEPA filter, and the fan 13 is configured between the air outlet 28 of the ULPA ultra-efficient air filter or the air outlet 52 of the HEPA filter and the sterilized air outlet.

The second ultraviolet lamp tube is configured above or in the instantaneous sterilization device 2, and can directly irradiate the clean water spray liquid 33 completely.

The third ultraviolet lamp tube is configured above or in the instantaneous sterilization device 2, and can directly irradiate the clean water 32 completely.

In this embodiment, the ultraviolet disinfection lamps are configured on the basis of FIG. 16, so as to sterilize the clean water spray liquid 33 and the clean water 32 in the water-washing type spray device 31 by using ultraviolet rays, and achieve instantaneous sterilization by combining with the ULPA ultra-efficient air filter 11 or the HEPA high efficiency particle air filter 49. The instantaneous sterilization device provided by FIG. 16 is very suitable for cheap primary air systems for household and commercial sterilization.

Figure 18:
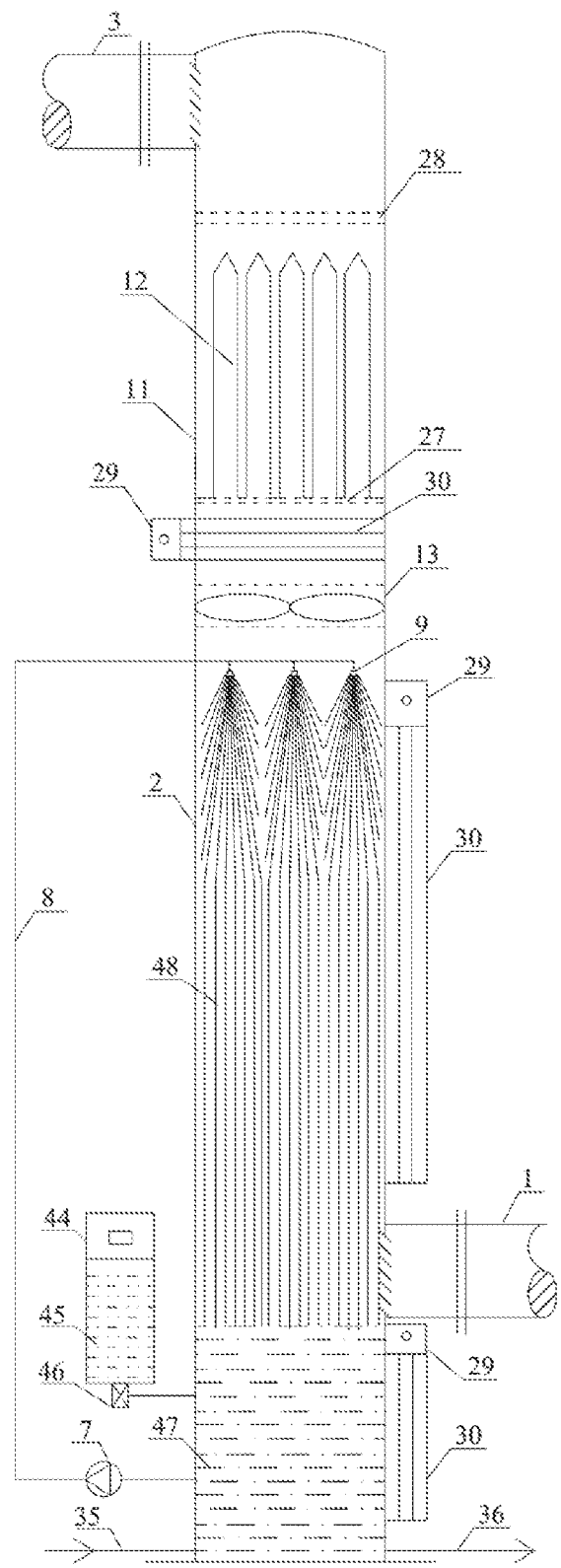
FIG. 18 is a schematic diagram of instantaneous sterilization through the combination of hydrogen peroxide silver ion air-liquid, and the ULPA ultra-efficient air filter or the HEPA high efficiency particle air filter combined with ultraviolet rays according to the instantaneous sterilization system for ventilation and air conditioning provided by the present application.

FIG. 18 is configured with an ultraviolet disinfecting device 29, an ultraviolet lamp tube 30, a fan 13 and one of the ULPA ultra-efficient air filter 11 or the HEPA high efficiency particle air filter 49 on the basis of FIG. 3, wherein the ultraviolet disinfecting device 29 comprises a first ultraviolet disinfecting device, a second ultraviolet disinfecting device and a third ultraviolet disinfecting device, and the ultraviolet lamp tube 30 comprises a first ultraviolet lamp tube, a second ultraviolet lamp tube and a third ultraviolet lamp tube.

The first ultraviolet disinfecting device, the second ultraviolet disinfecting device and the third ultraviolet disinfecting device are respectively corresponding to the first ultraviolet lamp tube, the second ultraviolet lamp tube and the third ultraviolet lamp tube 30, and connected. The ULPA ultra-efficient air filter 11 or the HEPA high efficiency particle air filter 49 is configured between the first ultraviolet lamp tube 30 and the sterilized air outlet 3, the first ultraviolet lamp tube 30 is configured between the fan 13 and the air inlet 27 of the HEPA filter, and the fan 13 is configured between the first ultraviolet lamp tube 30 and the nozzle 9.

The second ultraviolet lamp tube 30 is configured above or in the instantaneous sterilization device 2, and can directly irradiate all the hydrogen peroxide silver ion spray liquid 48 completely.

The third ultraviolet lamp tube 30 is configured above or in the instantaneous sterilization device 2, and can directly irradiate all the hydrogen peroxide silver ion solution 47 completely.

FIG. 18 is very suitable for primary air systems for household and commercial sterilization, and has certain practical and commercial values.

Figure 19:
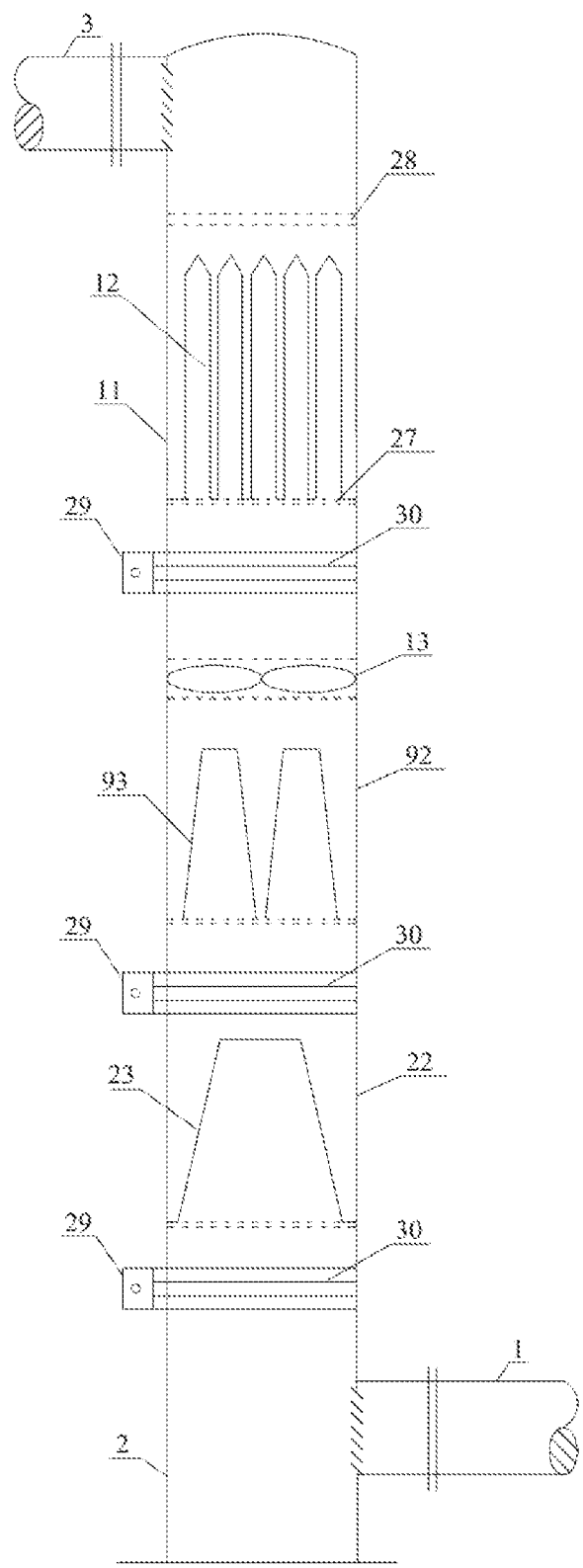
FIG. 19 is an embodiment of instantaneous sterilization by configuring a medium-efficiency filter and a primary filter for the ULPA ultra-efficient air filter or HEPA high efficiency particle air filter according to the instantaneous sterilization system for ventilation and air conditioning provided by the present application.

FIG. 19 is configured with one of the ULPA ultra-efficient air filter 11 or the HEPA high efficiency particle air filter 49 on the basis of FIG. 1 and further provided with an ultraviolet disinfecting device 29, an ultraviolet lamp tube 30, a medium-efficiency filter 92, a primary filter 22 and the fan 13, wherein the ultraviolet disinfecting device 29 comprises a first ultraviolet disinfecting device, a second ultraviolet disinfecting device and a third ultraviolet disinfecting device, and the ultraviolet lamp tube 30 comprises a first ultraviolet lamp tube, a second ultraviolet lamp tube and a third ultraviolet lamp tube.

The first ultraviolet disinfecting device, the second ultraviolet disinfecting device and the third ultraviolet disinfecting device are respectively corresponding to the first ultraviolet lamp tube, the second ultraviolet lamp tube and the third ultraviolet lamp tube, and connected. The medium-efficiency filter 92 is internally provided with a medium-efficiency filter element screen 93, and the primary filter 22 is internally provided with a primary filter element screen 23.

The ULPA ultra-efficient air filter 11 or the HEPA high efficiency particle air filter 49 is configured between the first ultraviolet lamp tube and the sterilized air outlet 3, the first ultraviolet lamp tube is configured above the fan 13 and between the air inlet 27 of the HEPA filter or the air inlet 51 of the HEPA filter, and the fan 13 is configured between the first ultraviolet lamp tube 30 and the medium-efficiency filter 92.

The second ultraviolet lamp tube is configured between the medium-efficiency filter 92 and the primary filter 22, and an air inlet of the medium-efficiency filter 92 is connected with the second ultraviolet lamp tube.

The third ultraviolet lamp tube is configured between the primary filter 22 and the air inlet 1, the primary filter 22 is configured between the second ultraviolet lamp tube 30 and the third ultraviolet lamp tube 30, and the third ultraviolet lamp tube is connected with an air inlet of the primary filter 22.

In this embodiment, air is sucked in through the air inlet 1. Firstly, dust in the air is filtered by the primary filter element screen 23. After the dust is removed and the leaked smaller particles and air that are not blocked by the primary filter element screen 23 pass through the primary filter 22, they are sucked into the medium-efficiency filter element screen 93, and the smaller particles that are not blocked and filtered by the primary filter element screen 23 will be blocked and filtered in the medium-efficiency filter 92. The finer particles, bacteria and viruses that are not blocked by the medium-efficiency filter 92 are finally sucked into the ULPA ultra-efficient filter element 12 internally provided in the ULPA ultra-efficient air filter 11 or the HEPA filter element screen 50 internally provided in the HEPA high efficiency particle air filter 4. After the fine bacteria and viruses are blocked and filtered by the ULPA ultra-efficient filter element 12 or the HEPA filter element screen 50, the clean sterilized air is discharged from the sterilized air outlet 3.

Bacteria and viruses that are blocked and remained in the primary filter element screen 23 will be sterilized by the third ultraviolet lamp tube. Bacteria and viruses that are blocked and remained in the medium-efficiency filter element screen 93 will be sterilized by the second ultraviolet lamp tube. Bacteria and viruses that are blocked and remained in the ULPA ultra-efficient filter element 12 or the HEPA filter element screen 50 will be sterilized by the first ultraviolet lamp tube.

This embodiment is an instantaneous sterilization system for ventilation and air conditioning, which adopts all filters and is configured with ultraviolet rays for sterilization, which is convenient for application due to the simple structure.

Figure 20:
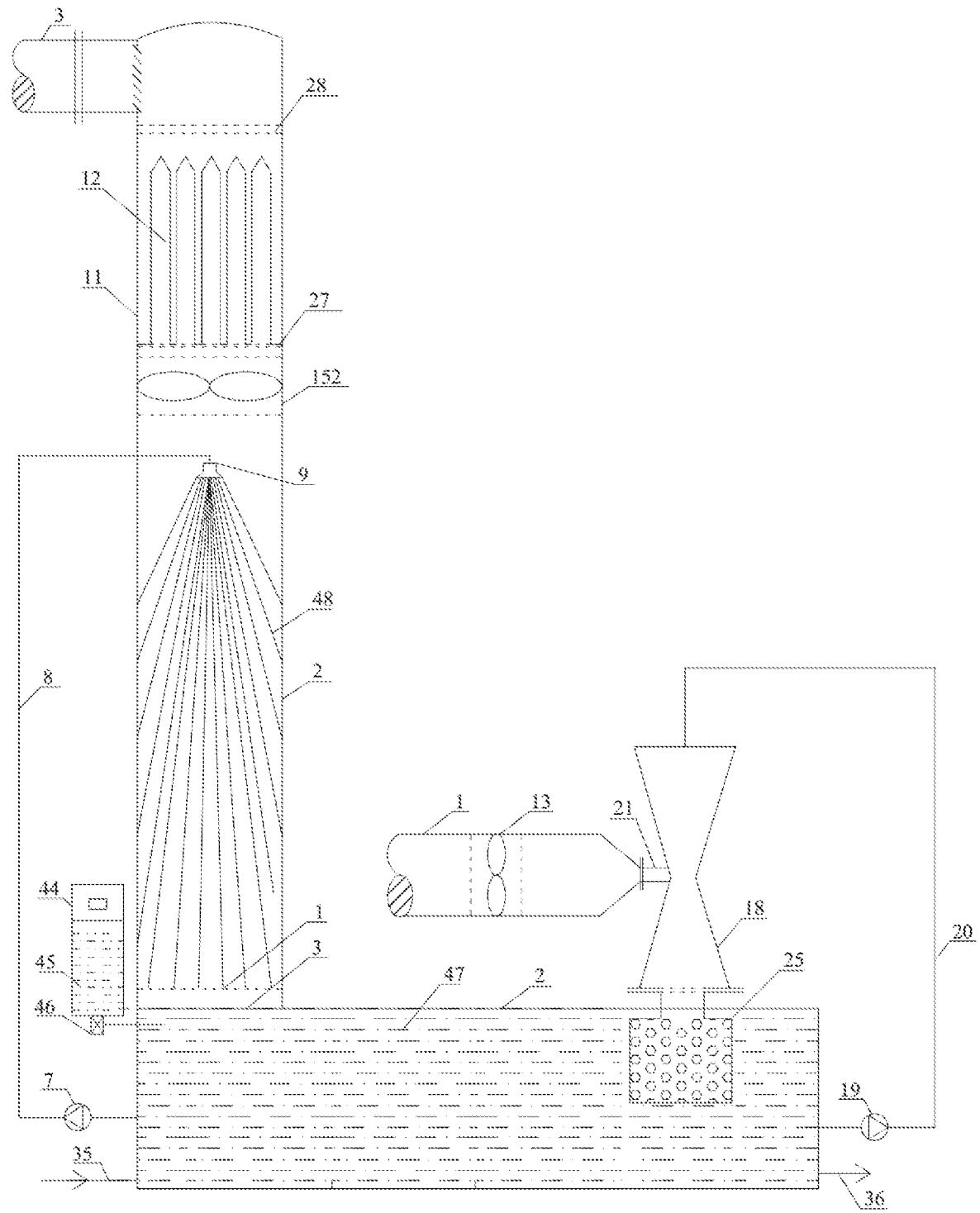
FIG. 20 is an embodiment of instantaneous sterilization by vertical spraying and horizontal air-liquid mixing disinfection according to the instantaneous sterilization system for ventilation and air conditioning provided by the present application.

In FIG. 20, two instantaneous sterilization devices 2 are adopted, which are respectively a first instantaneous sterilization device and a second instantaneous sterilization device, wherein the second instantaneous sterilization device is vertically configured above a first end of the first instantaneous sterilization device, and the first instantaneous sterilization device is horizontally configured.

The second instantaneous sterilization device comprises the spray pump 7, the nozzle 9, a booster fan 152 and one of the ULPA ultra-efficient air filter 11 or the HEPA high efficiency particle air filter 49. The first instantaneous sterilization device comprises a Venturi air-liquid mixer 18, a Venturi circulating pump 19, an immersion air-liquid mixer 25, the hydrogen peroxide silver ion liquid device 44 and the fan 13. The hydrogen peroxide silver ion solution 47 is added in the hydrogen peroxide silver ion liquid device 44.

The output end of the spray pump 7 in the second instantaneous sterilization device is connected with the nozzle 9 and sprays the hydrogen peroxide silver ion spray liquid 48. The input end of the spray pump 7 is connected with the first instantaneous sterilization device and communicated with the hydrogen peroxide silver ion solution 47 in the first instantaneous sterilization device. The booster fan 152 is configured between the ULPA ultra-efficient air filter 11 and the nozzle 9, or configured between the HEPA high efficiency particle air filter 49 and the nozzle 9. The ULPA ultra-efficient air filter 11 or the HEPA high efficiency particle air filter 49 is configured between the booster fan 152 and the sterilized air outlet 3. The air inlet 27 of the HEPA filter or the air inlet 51 of the HEPA filter is connected with the air exhaust end of the fan 13.

An outlet of the Venturi air-liquid mixer 18 in the first instantaneous sterilization device is connected with an inlet of the immersion air-liquid mixer 25, and the immersion air-liquid mixer 25 is immersed in the hydrogen peroxide silver ion solution 47 and fixed to a bottom portion of a second end of the first instantaneous sterilization device. An inlet of the Venturi air-liquid mixer 18 is connected with an output end of the Venturi circulating pump 19, and an input end of the Venturi circulating pump 19 is connected with the first instantaneous sterilization device and communicated with the hydrogen peroxide silver ion solution 47. The air passes through the air inlet 1 and the fan 13, and is connected with a Venturi intakeport 21, and is connected with the Venturi intakeport 21 through the air exhaust end of the fan 13. The hydrogen peroxide silver ion liquid device 44 is internally provided with the hydrogen peroxide silver ion liquid 45 and communicated with the hydrogen peroxide silver ion solution 47 in the first instantaneous sterilization device.

In this embodiment, the Venturi intakeport 21 is configured with the fan 13 to increase the air intake of the Venturi air-liquid mixer 18. In the related art, the Venturi intakeport 21 is not configured with any fan, but a medium flow input from the inlet of the Venturi air-liquid mixer 18 causes a negative pressure formed at the Venturi intakeport 21 to suck air. A vacuum degree of the Venturi intakeport 21 is adjusted by a liquid flow of the Venturi circulating pump 19 to change the air intake of the Venturi intakeport 21. In this application, the fan 13 is arranged at the Venturi intakeport 21, and the fan is used to increase the air intake of the Venturi intakeport 21 and improve the air-liquid mixing amount, so as to improve the ventilation circulation of the ventilation and air conditioning system. The ventilation and air conditioning system often needs large-volume circulation ventilation. In the related art, with the increase of the medium flow at the inlet of the Venturi air-liquid mixer 18, a Venturi circulating pump 19 with very large circulation volume needs to be configured, resulting in very large electric power of the Venturi circulating pump 19, which is not conducive to the energy-saving operation of the ventilation and air conditioning system.

Figure 21:
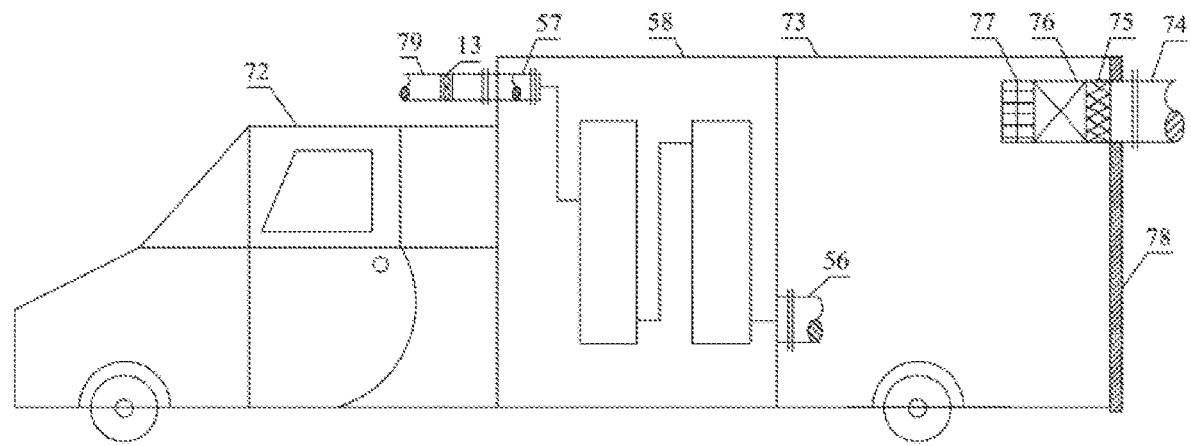
FIG. 21 is a schematic diagram of a negative-pressure harmless ambulance provided by the present application.

FIG. 21 shows an instantaneous sterilization system 58 constituted by any one of FIG. 1 to FIG. 20, and a negative-pressure harmless ambulance 72 composed of an ambulance negative-pressure cabin 73, a negative-pressure ambulance air inlet 74 and a negative-pressure air outlet 79 is provided.

The instantaneous sterilization system 58 is an instantaneous sterilization system with an instantaneous sterilization system air inlet 56 as an air input end, an instantaneous sterilization system air outlet 57 as an output end of the instantaneous sterilization system, and the instantaneous sterilization system 58 is an instantaneous sterilization system for ventilation and air conditioning as shown in any one of FIGS. 1 to 20. The instantaneous sterilization system 58 is communicated with the ambulance negative-pressure cabin 73 through the instantaneous sterilization system air inlet 56, passes through a negative-pressure ambulances air-conditioning air port 77, an ambulance air-conditioning surface cooler 76 and a ventilation dust filtrating screen 75, and communicated with the outdoor air from a negative-pressure ambulance air inlet 74 and serves as an air input end of the negative-pressure ambulance. Cold and heat sources of an air-conditioning system of the ambulance may be used as cold and heat sources of the ambulance air-conditioning surface cooler 76 to provide cooling and heating for the ambulance, but a cab and the ambulance negative-pressure cabin 73 should be sealed and isolated to prevent the spread of viruses. The instantaneous sterilization system air outlet 57 is communicated with atmosphere through the negative-pressure air outlet and serves as a harmless discharge end of the negative-pressure harmless ambulance 72. The fan 13 configured between the instantaneous sterilization system air outlet 57 and the negative-pressure air outlet 79 may either be provided or not provided according to wind volume and wind pressure situations of the fan inside the instantaneous sterilization system 58, depending on whether negative-pressure requirements are met. If the instantaneous sterilization system 58 has already met the negative-pressure requirements of the ambulance, the fan 13 may not be provided. Once the fan inside the instantaneous sterilization system 58 cannot satisfy the negative-pressure requirements of the ambulance, the fan 13 is provided, and proper wind pressure and wind pressure are selected to meet the overall negative-pressure requirements of the ambulance. The present application not only obtains the negative pressure, but also realizes the harmless discharge of the ambulance, which will not pollute the atmosphere of urban streets where patients with infectious diseases are rescued and transported, and will not cause cross-infection between next rescued patient and the previous patients. As the instantaneous sterilization system 58 of the present application has sterilized the ambulance, it is of great significance to the prevention and control of the epidemic situation in novel coronavirus.

Figure 22:
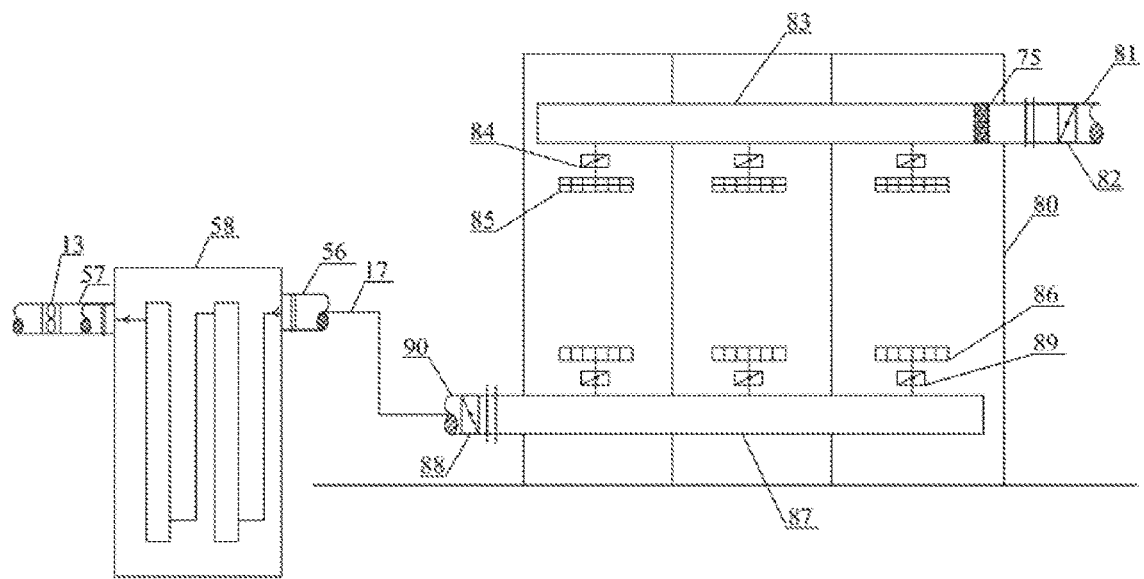
FIG. 22 is a schematic diagram of a negative-pressure harmless discharge contagious ward provided by the present application.

FIG. 22 shows a negative-pressure harmless discharge contagious ward constructed by arranging a negative-pressure harmless contagious ward 80 and the instantaneous sterilization system 58 on the basis of FIG. 21.

In FIG. 22, the instantaneous sterilization system 58 passes through the instantaneous sterilization system air inlet 56, an air duct 17, a negative-pressure harmless discharge contagious ward air-return interface 90 and a contagious ward air-return duct check valve 88, is connected with a contagious ward air-conditioning air-return duct 87, passes through a contagious ward air-conditioning air-return port check valve 89 and is communicated with the negative-pressure harmless contagious ward 80, and serves as a contagious ward return air outlet.

A contagious ward air-conditioning air outlet port 85 passes through a contagious ward air-conditioning air-return port check valve 84 and a contagious ward air conditioning air-delivery duct 83, the ventilation dust filtrating screen 75, a contagious ward air duct check valve 82 and a contagious ward air inlet 81, communicated with atmosphere, and serves as an air input end of the negative-pressure harmless contagious ward.

The instantaneous sterilization system 58 is communicated with the atmosphere through the instantaneous sterilization system air outlet 57 and serves as a harmless discharge output end of the negative-pressure harmless contagious ward 80. The fan 13 is configured at the instantaneous sterilization system air outlet 57 in order to ensure a negative-pressure degree of the negative-pressure harmless discharge contagious ward, and the fan 13 may not be disposed if a fan system in the instantaneous sterilization system 58 can satisfy the negative pressure of the negative-pressure harmless discharge contagious ward.

The negative-pressure harmless discharge contagious ward in this embodiment can not only ensure that medical personnel are not infected by patients, but also ensure that air emitted by the contagious ward is discharged harmlessly, does not pollute the atmosphere of surrounding cities, and is very suitable for being used as a rescue hospital in cities with high virus epidemic situations.

Figure 23:
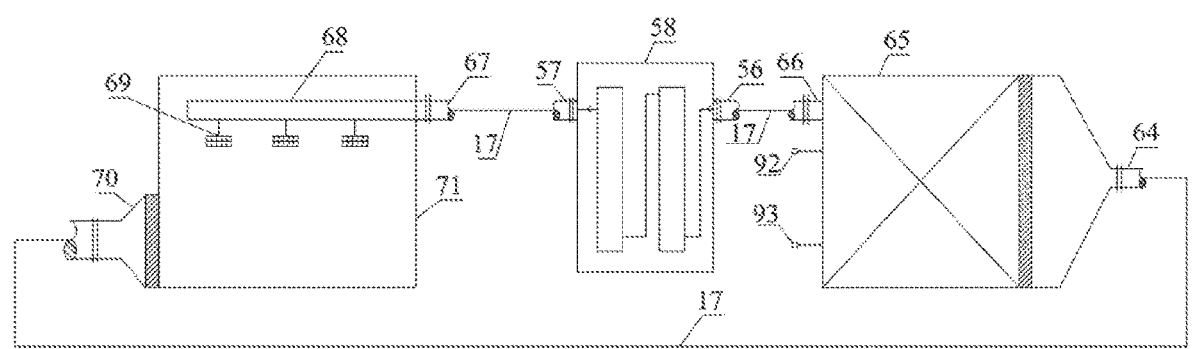
FIG. 23 is a schematic diagram of a sterilization air-conditioning system provided by the present application.

FIG. 23 shows an embodiment of a sterilization system for ventilation and air conditioning provided by the present application. In FIG. 23, a sterilization air-conditioning system is formed by arranging an air-conditioning unit 65 and a sterilization air-conditioning house 71 on the basis of FIG. 22. The air-conditioning unit 65 configured in FIG. 23 is hermetically connected with the instantaneous sterilization system 58 through an air-conditioning unit air outlet 66, the air pipe 17 and the instantaneous sterilization system air inlet 56, is hermetically connected with the air-conditioning air-delivery duct 68 through the instantaneous sterilization system air outlet 57, the air pipe 17 and a sterilization air-conditioning air-inlet interface 67, is communicated with the sterilization air-conditioning house 71 through the air-conditioning air-delivery duct 68 and an air-conditioning air port 69, and serves as a closed air-conditioning air supply system.

The sterilization air-conditioning house 71 is hermetically connected with the air-conditioning unit air inlet 64 through a sterilization air-conditioning room air-return port 70 and the air pipe, and serves as an air-conditioning sterilization circulating air-return system. The system is very suitable for being used as a central air-conditioning sterilization system to create a sterile public place.

The sterilization system for ventilation and air conditioning provided in FIG. 23 can realize real-time air-conditioning sterilization circulating ventilation, and can be operated safely as long as the sterilization air-conditioning room air-return port 70 is reasonably selected and designed to meet the requirements of infection airflow distribution. FIG. 22 shows only a circulating air-conditioning system, which is not equipped with a primary air system, and this embodiment may be configured with a primary air system, or with the sterilization primary air system of FIG. 21. The ventilation and air conditioning systems provided in this application is a sterilization central air-conditioning system. When the air-return ports and air outlets in the existing supermarkets, marketplaces, movie theaters, and other places are configured reasonably to meet the airflow distribution of infectious medicine, and then the sterilization system for ventilation and air conditioning of FIG. 23 is configured, real-time sterilization in manned places can be realized.

Figure 24:
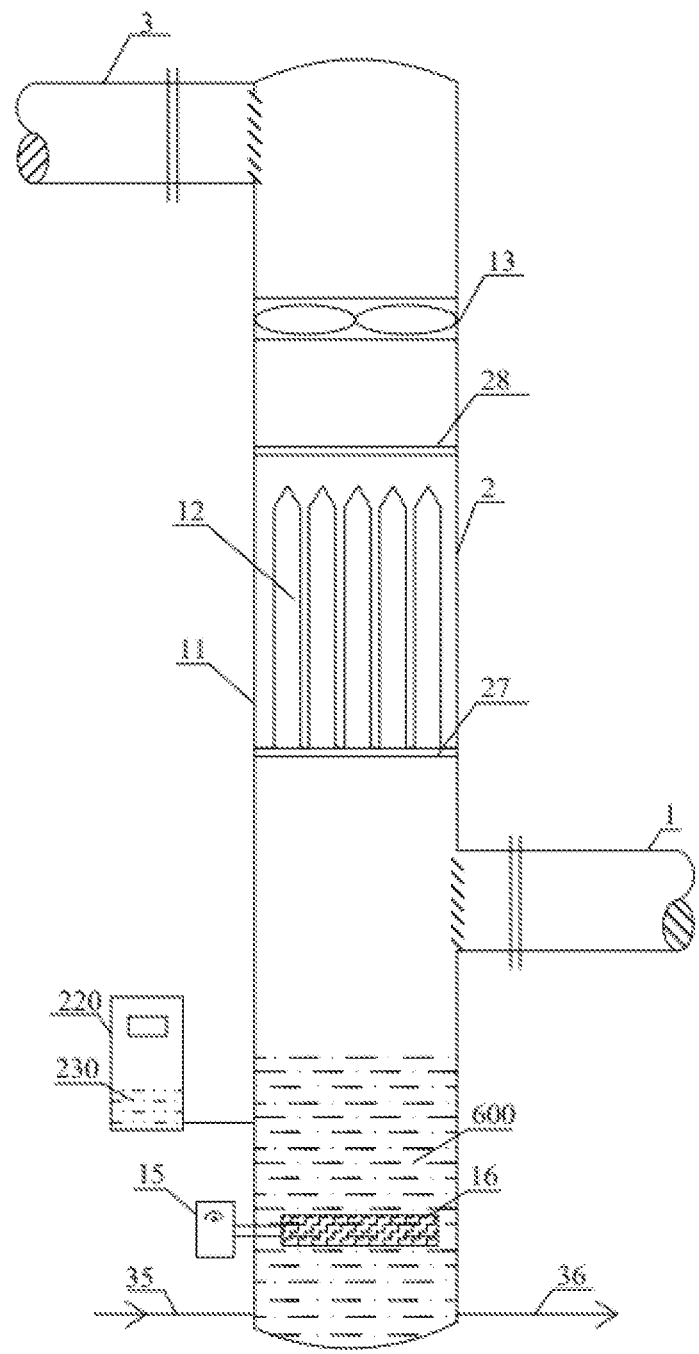
FIG. 24 is a schematic diagram of an instantaneous sterilization system for ventilation and air conditioning configured with the ULPA ultra-efficient air filter or the HEPA high efficiency particle air filter and disinfecting by spraying a chlorine dioxide solution provided by an embodiment.

In one embodiment, as shown in FIG. 24, the instantaneous sterilization device 2 is configured with a chlorine dioxide generator 220, a dioxide peroxide liquid 230 is prepared by the chlorine dioxide generator 220, and the dioxide peroxide liquid 230 is supplied to a chlorine dioxide solution 600 in the instantaneous sterilization device 2 by a control system of the chlorine dioxide generator 220. As the ultrasonic atomizer 15 and the ultrasonic generator 16 are configured to the chlorine dioxide solution 600 in the instantaneous sterilization device 2, the ultrasonic atomizer 15 outputs a high-frequency current with an ultrasonic frequency, and the piezoelectric ceramic in the ultrasonic generator 16 generates an ultrasonic vibration, so that the chlorine dioxide solution 600 around the ultrasonic generator 16 is atomized, the chlorine dioxide solution 600 is atomized to generate a large amount of chlorine dioxide molecules which drift away the chlorine dioxide solution 600, and the chlorine dioxide molecules float on the surface of the ULPA ultra-efficient filter element 12 of the ULPA ultra-efficient air filter 11 or the HEPA filter element screen 50 of the HEPA high efficiency particle air filter 49. The chlorine dioxide is a modern disinfection product which is recognized in the world as the safest and most safe disinfectant for quickly killing virus spores and harmless to human bodies. The large number of bacteria and viruses accumulated on the surface of the ULPA ultra-efficient filter element 12 of the ULPA ultra-efficient air filter 11 or the HEPA filter element screen 50 of the HEPA high efficiency particle air filter 49 will be killed by the chlorine dioxide after contacting with the large number of atomized floating chlorine dioxide molecules. Although the chlorine dioxide cannot kill the viruses instantaneously, due to the instantaneous blocking and filtering effect of the ULPA ultra-efficient air filter 11 or the HEPA high efficiency particle air filter 49, a large number of captured bacterial and virus particles will be inactivated by the chlorine dioxide after a certain disinfection time. The above disinfection and sterilization process firstly uses the ULPA ultra-efficient air filter 11 or the HEPA high efficiency particle air filter 49 to instantaneously block the bacteria and the viruses, and then uses the chlorine dioxide to sterilize within a standard disinfection time. In a word, in this embodiment, the first step is to block the virus particles instantaneously by a filtration technology; and the second step is to use a disinfectant to kill the bacteria and the viruses slowly, and finally realize the instantaneous sterilization and real-time sterilization of the ventilation and air conditioning system. The fan 13 is configured between the air outlet 28 of the ULPA ultra-efficient air filter and the sterilized air outlet 3, or configured between the air outlet 52 of the HEPA filter and the sterilized air outlet 3, and finally, the sterilized clean air is discharged from the sterilized air outlet 3. The instantaneous sterilization device provided by FIG. 24 has a simple structure, and is suitable for families, negative-pressure ambulances, single contagious wards and various vehicles requiring low ventilation volume.

In the related art, there are no successful methods of compressing or storing chlorine dioxide, whether alone or combined with other gases. Because the chlorine dioxide is prone to explosion, it must be manufactured at the place of use. Therefore, the dioxide peroxide is mostly in the form of powdered drug or effervescent tablets. When a concentration of a chlorine dioxide aqueous solution is lower than 8-10 g/L, a high vapor pressure enough to cause explosion danger may not be produced. In practice, the concentration of the chlorine dioxide rarely exceeds 4 g/L, generally in a range of 0.1-5.0 mg/L. The chlorine dioxide gas is easily soluble in water, with a solubility five times that of chlorine gas. The chlorine dioxide gas is dissolved in water to form a yellow-green solution, which has a pungent odor similar to chlorine gas.

In the dioxide peroxide generator 220 shown in FIG. 24, a hydrochloric acid reacts with sodium chlorate to generate dioxide peroxide. In one embodiment, the dioxide peroxide generator 220 comprises a feeding system, a reaction system, a control system and a safety system, which can realize the object of automatically preparing and adding chlorine dioxide to the instantaneous sterilization system.

In FIG. 24, the tap water is supplied to the sterilization device through the tap water interface 35, and the waste chlorine dioxide solution 600 is discharged through the waste liquid discharge port 36. If automatic control devices are arranged on the tap water interface 35 and the waste liquid discharge port 36, automatic water replenishing and waste liquid discharge are achieved, and an unmanned intelligent sterilization system is achieved.

Figure 25:
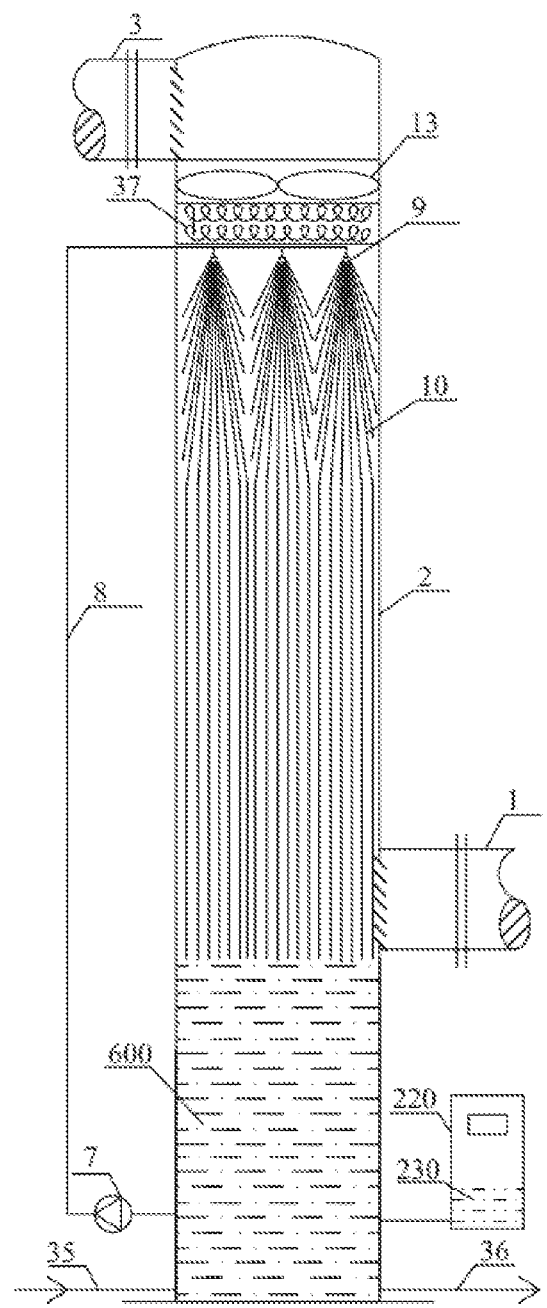
FIG. 25 is a schematic diagram of an instantaneous sterilization system for ventilation and air conditioning provided by an embodiment.

In FIG. 25, the instantaneous sterilization system for ventilation and air conditioning comprises the air inlet 1, the instantaneous sterilization device 2, the sterilized air outlet 3, a chlorine dioxide solution 600, the spray pump 7, the spray pipe 8, the nozzle 9, the fan 13, a chlorine dioxide generator 220 and a chlorine dioxide solution 230.

When running, the spray pump 7 sucks in the dioxide peroxide solution 600 in the instantaneous sterilization device 2 and conveys the same to a plurality of groups of nozzles 9 through the spray pipe 8, and sprays a dioxide peroxide spray liquid 10 downwards. After the fan 13 works, the instantaneous sterilization device 2 forms a negative pressure, air contaminated by bacteria and viruses is sucked in from the air inlet 1, the dense chlorine dioxide spray liquid 10 and the contaminated air forcedly sucked by the fan 13 reversely collide and rub for washing and disinfection. If the instantaneous sterilization device 2 has a preset vertical height, the disinfection time can be prolonged, and the effect of killing the bacteria and the viruses can be improved. The sterilized air is discharged through the sterilized air outlet 3. In order to prevent the dioxide peroxide spray liquid 10 from drifting out of the sterilized air outlet 3 and entering the air, an air-water separating device 37 is configured to block the chlorine dioxide fog drops and return the chlorine dioxide fog drops into the sprayed dioxide peroxide spray liquid 10, and the clean sterilized air is discharged from the sterilized air outlet 3.

Figure 26:
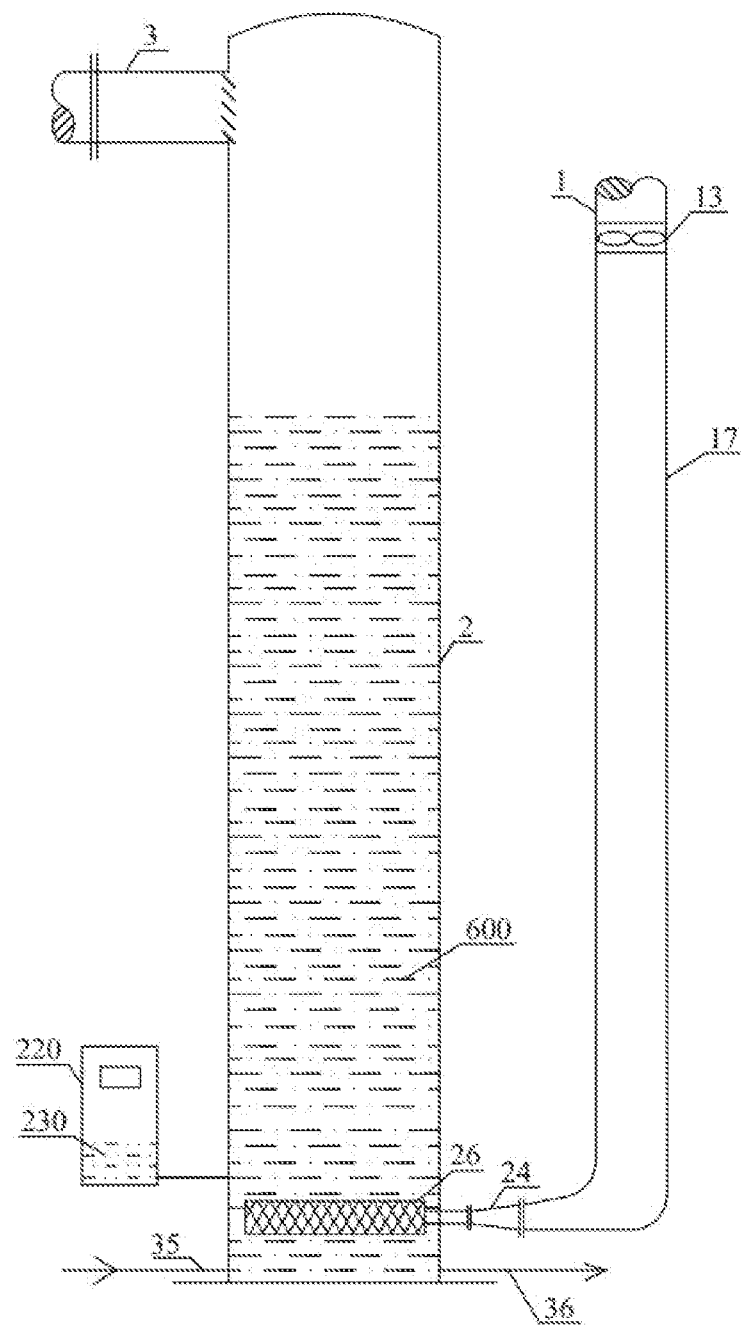
FIG. 26 is a schematic diagram of an instantaneous sterilization system for ventilation and air conditioning disinfecting by dioxide peroxide microporous air-liquid mixing provided by an embodiment.
Figure 27:
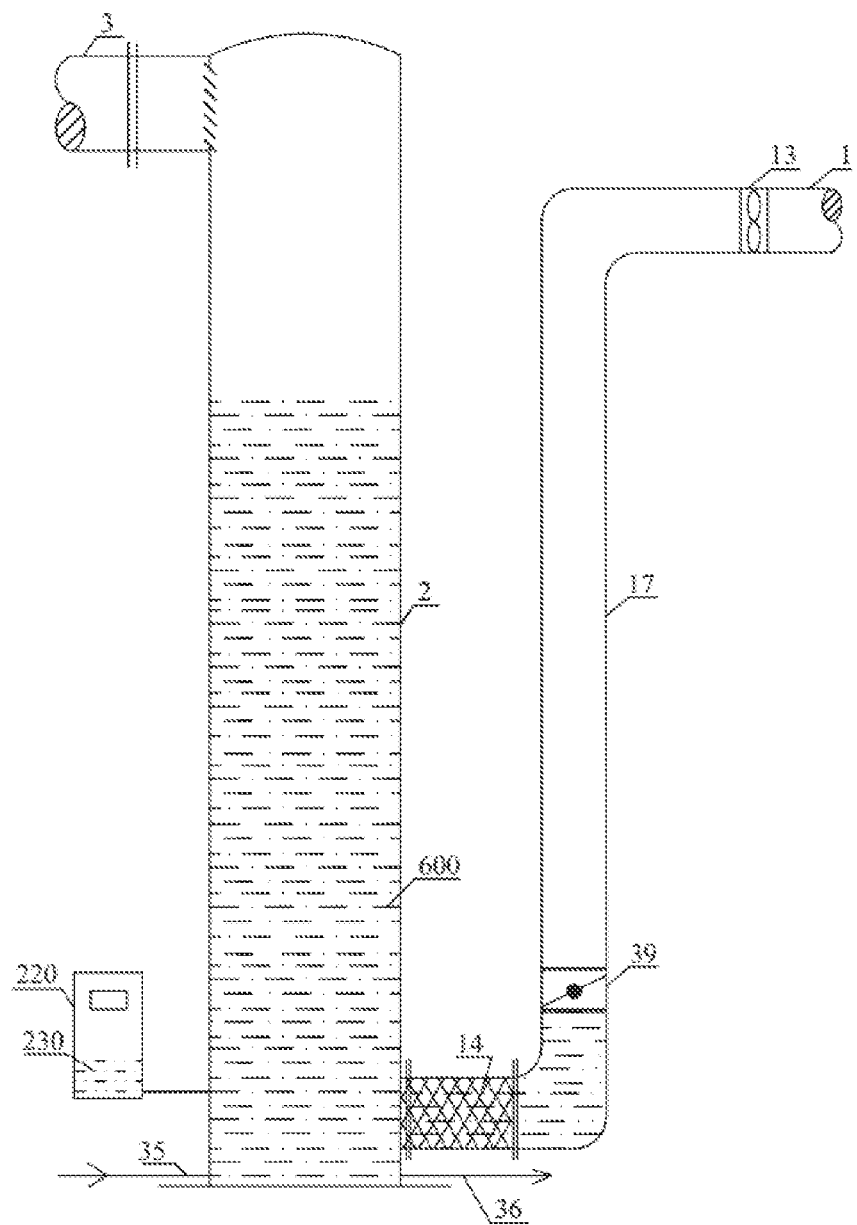
FIG. 27 is a schematic diagram of an instantaneous sterilization system for ventilation and air conditioning disinfecting by dioxide peroxide pipeline air-liquid mixing provided by an embodiment.
Figure 28:
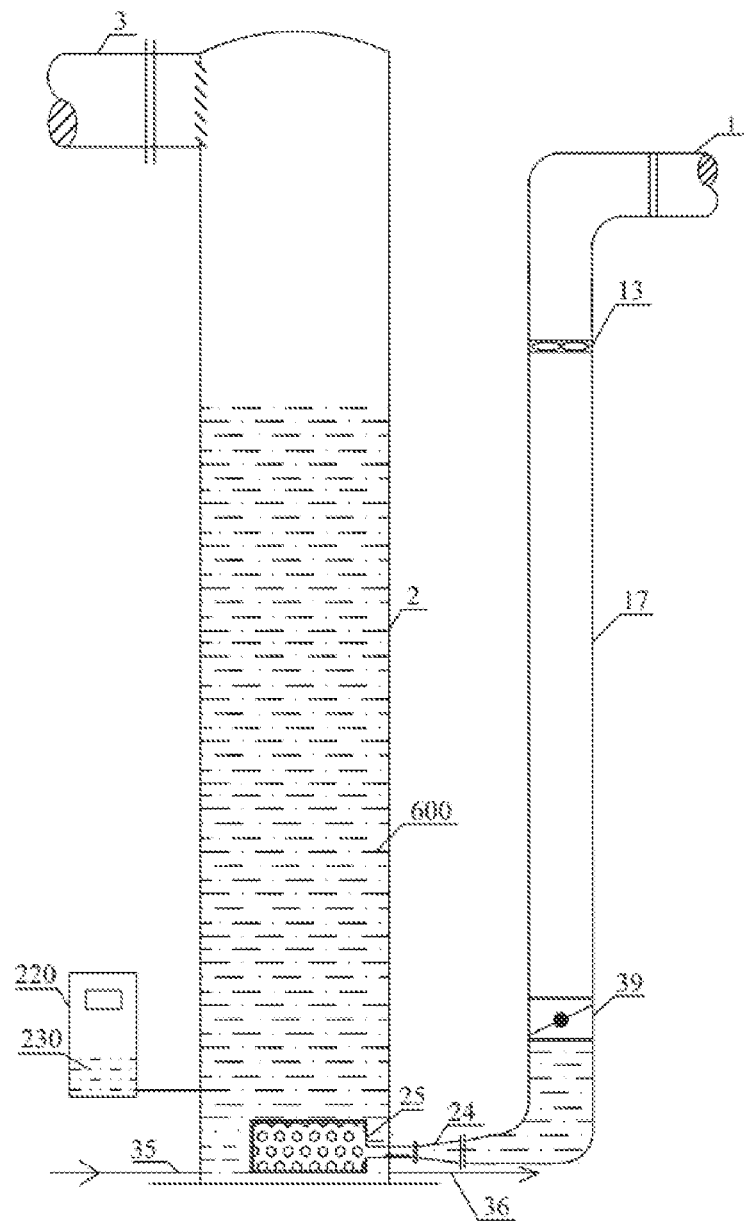
FIG. 28 is a schematic diagram of an instantaneous sterilization system for ventilation and air conditioning for instantaneous sterilization through disinfecting by dioxide peroxide immersion air-liquid mixing provided by an embodiment.
Figure 29:
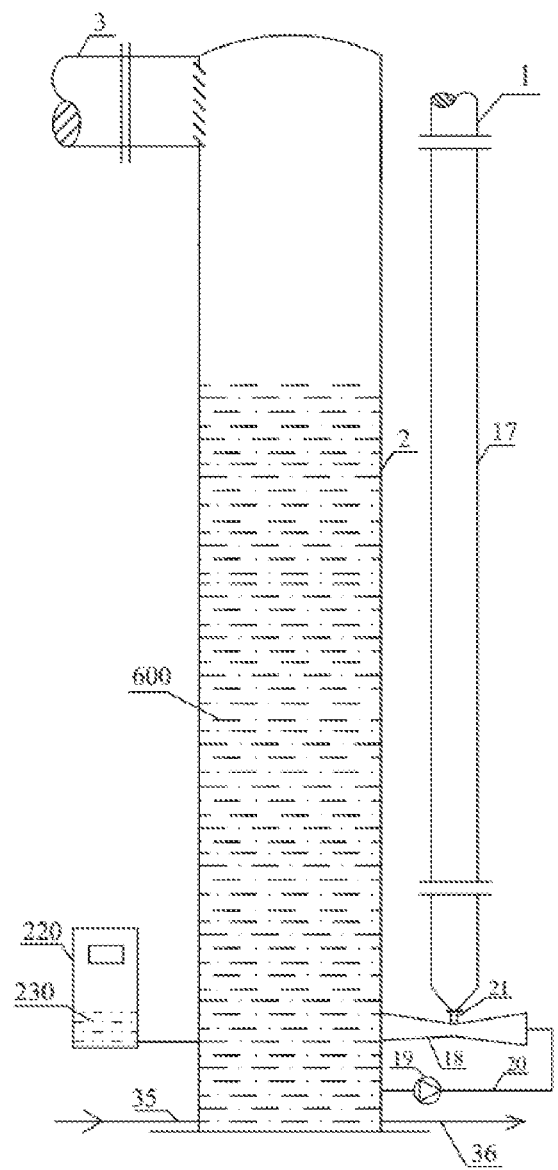
FIG. 29 is a schematic diagram of an instantaneous sterilization system for ventilation and air conditioning for instantaneous sterilization through disinfecting by dioxide peroxide Venturi pipe air-liquid mixing provided by an embodiment.
Figure 30:
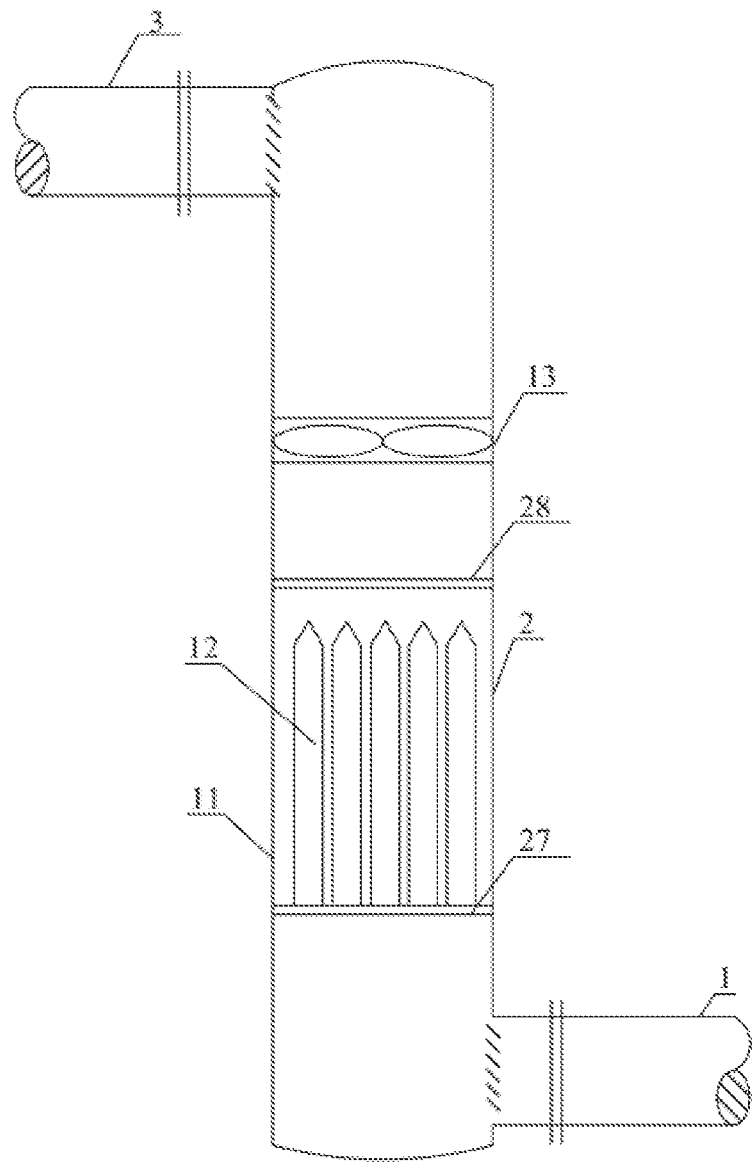
FIG. 30 is a schematic diagram of an instantaneous sterilization device provided by still another embodiment of the present application.
Figure 31:
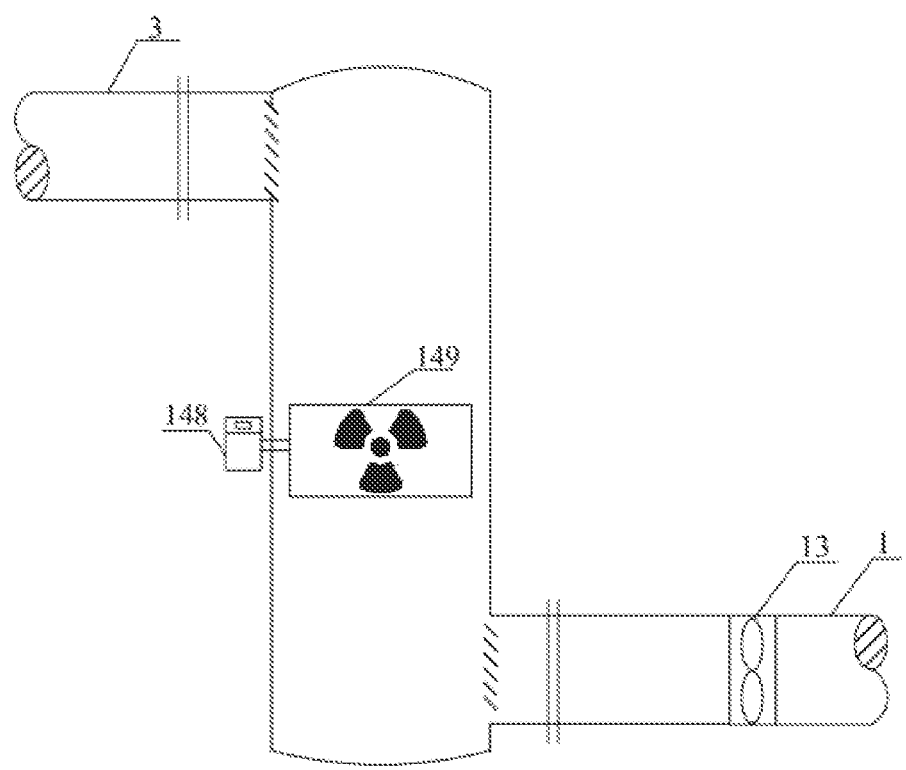
FIG. 31 is a schematic diagram of an instantaneous sterilization device provided by another embodiment of the present application.

In one embodiment, the instantaneous sterilization system for ventilation and air conditioning shown in FIG. 26 has a sterilization speed which is not as fast as that configured with the ULPA ultra-efficient air filter 11 or the HEPA high efficiency particle air filter 49 combined with the chlorine dioxide solution 600, but is suitable for use in situations with large air volume and low sterilization requirements due to the small wind resistance.

In one embodiment, the instantaneous sterilization system for ventilation and air conditioning shown in FIG. 26 comprises the air inlet 1, the instantaneous sterilization device 2, the sterilized air outlet 3, a chlorine dioxide solution 600, the fan 13, a chlorine dioxide generator 220, a chlorine dioxide solution 230 and a microporous air-liquid mixer 26.

The microporous air-liquid mixer 26 is immersed in a bottom portion of the dioxide peroxide solution 600, an inlet of the microporous air-liquid mixer 26 is connected with the air exhaust end of the fan 13, and the air inlet end of the fan 13 is communicated with contaminated air through the air inlet 1. After the fan 13 is running, air containing bacteria and viruses is sucked from the air inlet 1 and sent into the microporous air-liquid mixer 26 via an air-liquid mixer interface 24, the air in the microporous air-liquid mixer 26 is cut into very fine air units, tiny bubbles are sprayed to the hydrogen dioxide peroxide solution 600 by the microporous air-liquid mixer 26, and the tiny bubbles float from bottom to top and move upwards in the dioxide peroxide solution 600 due to the fact that the mass of the air is smaller than that of the liquid. In the process of drifting, the bacteria and the viruses in the contaminated air are killed by the dioxide peroxide solution 600. The smaller the diameter of the bubbles, the better the friction disinfection effect between the bacteria, the viruses and the chlorine dioxide solution 600. The sterilized air is discharged out of the instantaneous sterilization device 2 through the sterilized air outlet 3, thus completing the function of killing the virus particles.

A liquid level of the chlorine dioxide solution 600 varies with a wind pressure of the fan 13, so that a certain distance height is kept between the liquid level of the dioxide peroxide solution 600 and the sterilized air outlet 3 to prevent the dioxide peroxide solution 600 from overflowing.

An instantaneous sterilization system for ventilation and air conditioning provided in FIG. 25 comprises the instantaneous sterilization device 2, the air inlet 1, the sterilized air outlet 3, a dioxide peroxide solution 600, the fan 13, a pipeline air-liquid mixer 14, a dioxide peroxide generator 220 and a dioxide peroxide liquid 230.

The pipeline air-liquid mixer 14 has substantially the same function as the microporous air-liquid mixer 26 shown in FIG. 26, except that the dioxide peroxide solution 600 is immersed in the pipeline air-liquid mixer 14, and the pipeline air-liquid mixer 14 is provided with an air cutting device capable of cutting air into fine air components. The air containing pollution is cut by the air cutting device and collided with the dioxide peroxide solution 600 in the pipeline air-liquid mixer 14 at high speed to move, and an air-liquid mixture is formed, so that the bacteria and viruses in the air are fully contacted, rubbed, washed and disinfected with the dioxide peroxide solution 600. Finally, the air-liquid mixture rotates at a high speed and enters the dioxide peroxide solution 600 through an outlet of the pipeline air-liquid mixer 14. The tiny bubbles continuously drift upwards in the dioxide peroxide solution 600, and the disinfected and sterilized air is discharged from the sterilized air outlet 3 to complete instantaneous sterilization.

The instantaneous sterilization system for ventilation and air conditioning provided by FIG. 28 comprises the instantaneous sterilization device, the air inlet 1, the sterilized air outlet 3, a dioxide peroxide solution 600, the fan 13, a dioxide peroxide generator 220, a dioxide peroxide liquid 230 and an immersion air-liquid mixer 25.

The instantaneous sterilization system for ventilation and air conditioning provided by FIG. 28 and the instantaneous sterilization systems for ventilation and air conditioning provided by FIG. 26 and FIG. 27 all adopt an air-liquid mixing disinfection mode. Contaminated air is sprayed into the immersion air-liquid mixer 25 through the air inlet 1 by the fan 13 at a high pressure. After the contaminated air is sprayed in the immersion air-liquid mixer 25, the air rotates at a high speed to spray a liquid-air state mixture to the dioxide peroxide solution 600 due to the internal structure of the immersion air-liquid mixer 25, and the rotation of the dioxide peroxide solution 600 drives the dioxide peroxide solution 600 to stir, so that the contaminated air is fully mixed with the dioxide peroxide solution 600 for disinfection, and then enters the dioxide peroxide solution 600 to float upwards and move and fully contact with the dioxide peroxide solution 600 to achieve further disinfection and sterilization.

The instantaneous sterilization systems for ventilation and air conditioning provided by FIG. 27 and FIG. 28 are suitable for application in systems with large ventilation volumes.

The instantaneous sterilization system for ventilation and air conditioning provided by FIG. 29 comprises the instantaneous sterilization device 2, the air inlet 1, the sterilized air outlet 3, a dioxide peroxide solution 600, a Venturi air-liquid mixer 18, a Venturi circulating pump 19, a dioxide peroxide generator 220 and a dioxide peroxide liquid 230.

The instantaneous sterilization system for ventilation and air conditioning in FIG. 29 uses a Venturi principle to realize the mixed disinfection of contaminated air and the chlorine dioxide solution 600 through the Venturi air-liquid mixer 18. When running, an input end of the Venturi circulating pump 19 sucks in the dioxide peroxide solution 600 in the sterilization device 2, then the dioxide peroxide solution 600 is input into an inlet of the Venturi air-liquid mixer 18 by a Venturi pump circulating pipe 20, and flows into the dioxide peroxide solution 600 of the Venturi air-liquid mixer 18 through the Venturi principle, which may lead to a vacuum negative pressure formed at the Venturi intakeport 21, then the contaminated air is sucked into the Venturi intakeport 21 through the air inlet 1, and a suction amount of the intakeport 21 is in proportion to a flow of the Venturi circulating pump 19. After the air enters the Venturi air-liquid mixer 18, according to the Venturi principle, the contaminated air and the dioxide peroxide solution 600 are fully mixed and exploded in the Venturi air-liquid mixer 18, a mixed air liquid formed by the contaminated air and the dioxide peroxide solution 600 is sprayed to the dioxide peroxide solution 600 by an outlet of the Venturi air-liquid mixer 18 and the contaminated air drifts upwards in the dioxide peroxide solution 600 for further sufficient sterilization via the dioxide peroxide solution 600. Finally, the air is discharged from the sterilized air outlet 3, so that the instantaneous sterilization is completed.

As shown in FIG. 30, the instantaneous sterilization system for ventilation and air conditioning further comprises one of the ULPA ultra-efficient air filter 11 or the high efficiency particle air filter 49 arranged in the instantaneous sterilization device 2. The ULPA ultra-efficient air filter 11 or the EHPA high efficiency particle air filter 49 is configured between the sterilized air outlet 3 and the air inlet 1, and the air inlet 27 of the ULPA ultra-efficient air filter or the air inlet 51 of the EHPA high efficiency particle air filter is connected with the air inlet 1. The air outlet 28 of the ULPA ultra-efficient air filter or the air outlet of the EHPA high efficiency particle air filter is connected with the sterilized air outlet 3. The sterilized air outlet 3 is communicated with the air, and serves as the output end of the instantaneous sterilization system for ventilation and air conditioning. The air inlet 1 is communicated with the air, and serves as the input end of the instantaneous sterilization system for ventilation and air conditioning.

As shown in FIG. 31, the instantaneous sterilization device 2 is further provided with one of an X-ray disinfecting device 148, an X-ray generator 149 or a γ-ray disinfecting device 150 and a γ-ray generator 151. The X-ray generator 149 or the γ-ray generator 151 is configured between the sterilized air outlet 3 and the air inlet 1, the X-ray disinfecting device 148 is connected with the X-ray generator 149 or the γ-ray disinfecting ilizing device 150 is connected with the γ-ray generator 151. The air inlet 1 is communicated with the air and serves as the input end of the instantaneous sterilization system for ventilation and air conditioning. The sterilized air outlet 3 is communicated with the air and serves as the output end of the instantaneous sterilization system for ventilation and air conditioning.

In one embodiment, the instantaneous sterilization device 2 is further configured with one of a hydrogen peroxide disinfectant, a formaldehyde disinfectant, a glutaraldehyde disinfectant, an ethylene oxide disinfectant, a peracetic acid disinfectant, a sodium hypochlorite disinfectant, a hypochloric acid disinfectant, a copper sulfate disinfectant, an ethanol disinfectant, a quaternary ammonium salt disinfectant, an isopropanol disinfectant, an n-propanol disinfectant and chlorine gas.

In other embodiments, the instantaneous sterilization device 2 is further provided with one of a plasma disinfecting device, a negative oxygen ion disinfecting device, a photo hydrogen ion disinfecting device, a photo oxygen ion disinfecting device and an electron accelerator irradiated disinfecting device.

To sum up, the combination of air-liquid mixing, spraying and spray liquid of the hydrogen peroxide silver ion solution 47 with the ULPA ultra-efficient air filter 11 or the HEPA high efficiency particle air filter 49 or the ultraviolet lamp tube 30 or the microwave or laser or ultraviolet or X-ray or γ-ray disinfection is designed to make the air in the ventilation and air conditioning system pass through the sterilization device at a very fast wind speed. No disinfectant can achieve the object of instantaneous sterilization. In order to realize the instantaneous sterilization of the ventilation and air conditioning system, the ULPA ultra-efficient air filter 11 or the HEPA high efficiency particle air filter 49 may be used to block the viruses instantaneously. Combined with the disinfection device of the present application, not only the bacteria and the viruses can be blocked instantaneously, but also bacteria and viruses can be prevented from multiplying, and finally, the object of instantaneous sterilization and real-time sterilization is achieved.

The invention claimed is:

1. An instantaneous sterilization system for ventilation and air conditioning, comprising:
    an air inlet (1), wherein the air inlet (1) is communicated with air, and configured to be an input end of the instantaneous sterilization system for ventilation and air conditioning;
    an instantaneous sterilization device (2), wherein the instantaneous sterilization device (2) is one or more of a chlorine dioxide disinfector, a hydrogen peroxide or hydrogen peroxide silver ion disinfector, an ultraviolet disinfector, an ULPA ultra-efficient air filter, a HEPA high efficiency particle air filter, a laser disinfector, a microwave disinfector, an infrared disinfector, an X-ray disinfector and a 7-ray disinfector, the air inlet (1) is configured at an input end of the instantaneous sterilization device (2), an output end of the instantaneous sterilization device (2) is provided with a sterilized air outlet (3), the sterilized air outlet (3) is configured at the output end of the instantaneous sterilization device (2), and the sterilized air outlet (3) is communicated with the air and serves as an output end of the instantaneous sterilization system for ventilation and air conditioning; and
    a fan (13), wherein an air inlet end of the fan (13) is connected with the the output end of the instantaneous sterilization device (2), and an air exhaust end of the fan (13) is connected with the sterilized air outlet (3);
    wherein the instantaneous sterilization device (2) is further provided with an ultrasonic atomizer (15), an ultrasonic generator (16) and a hydrogen peroxide silver ion liquid device (44), the instantaneous sterilization device (2) is internally provided with a hydrogen peroxide silver ion solution (47), the hydrogen peroxide silver ion liquid device (44) is internally provided with a hydrogen peroxide silver ion liquid (45), the hydrogen peroxide silver ion liquid device (44) is connected with the instantaneous sterilization device (2) and communicated with the hydrogen peroxide silver ion solution (47), and the ULPA ultra-efficient air filter (11) or the HEPA high efficiency particle air filter (49) is configured between the air inlet (1) and the output end of the instantaneous sterilization device (2);
    the ULPA ultra-efficient air filter (11) is provided with an air inlet (27) of the ULPA ultra-efficient air filter and an air outlet (28) of the ULPA ultra-efficient air filter, the HEPA high efficiency particle air filter (49) is provided with an air inlet (51) of the HEPA high efficiency particle air filter and an air outlet (52) of the HEPA high efficiently particle air filter, the air inlet (27) of the ULPA ultra-efficient air filter or the air inlet (51) of the HEPA high efficiency particle air filter is connected with the air inlet (1), the fan (13) is configured between the sterilized air outlet (3) and the ULPA ultra-efficient air filter (11) or configured between the sterilized air outlet (3) and the HEPA high efficiency particle air filter (49), and the air outlet (28) of the ULPA ultra-efficient air filter or the air outlet (52) of the HEPA high efficient particle air filter is connected with the air inlet of the fan (13); and
    the ultrasonic generator (16) is immersed in the hydrogen peroxide silver ion solution (47) and configured at an upper portion of the hydrogen peroxide silver ion solution (47), and a liquid level of the hydrogen peroxide silver ion solution (47) is below the air inlet (1).

* * * * *